United States Patent
Ke et al.

(10) Patent No.: US 12,351,655 B2
(45) Date of Patent: Jul. 8, 2025

(54) MECHANICALLY INTERLOCKED MOLECULES-BASED MATERIALS FOR 3-D PRINTING

(71) Applicant: Trustees of Dartmouth College, Hanover, NH (US)

(72) Inventors: Chenfeng Ke, Lebanon, NH (US); Qianming Lin, Lebanon, NH (US)

(73) Assignee: Trustees of Dartmouth College, Hanover, NH (US)

( * ) Notice: Subject to any disclaimer, the term of this patent is extended or adjusted under 35 U.S.C. 154(b) by 0 days.

(21) Appl. No.: 18/384,942

(22) Filed: Oct. 30, 2023

(65) Prior Publication Data

US 2024/0076415 A1    Mar. 7, 2024

Related U.S. Application Data

(60) Continuation of application No. 17/174,720, filed on Feb. 12, 2021, now Pat. No. 11,845,812, which is a
(Continued)

(51) Int. Cl.
   *C08B 37/16*    (2006.01)
   *A61K 47/69*    (2017.01)
   (Continued)

(52) U.S. Cl.
   CPC ...... *C08B 37/0015* (2013.01); *A61K 47/6951* (2017.08); *A61L 15/225* (2013.01);
   (Continued)

(58) Field of Classification Search
   CPC ..... C08B 37/0015; B33Y 10/00; B33Y 70/00; B33Y 80/00; A61K 47/6951; A61K 9/0024; A61K 9/06; A61L 15/225; A61L 15/26; A61L 15/28; A61L 15/60; A61L 26/0019; A61L 26/0023; A61L 26/008; A61L 27/18; A61L 27/20; A61L 27/26; A61L 27/52;
   (Continued)

(56) References Cited

PUBLICATIONS

Liu, K.L. et al. Supramolecular hydrogels based on cyclodextrin-polymer polypseudorotaxanes: materials design and hydrogel properties. Soft Matter, 2011, 7, 11290 (Year: 2011).*
(Continued)

*Primary Examiner* — Christina H. W. Rosebach
(74) *Attorney, Agent, or Firm* — Shackelford, McKinley & Norton, LLP

(57) ABSTRACT

Provided are supramolecular polypseudorotaxane hydrogel compositions and 3-D structures capable of reversible 3-D structural deformation which include (a) a solvent; (b) an at least partially linear polymer, where the polymer further comprises groups capable of covalent crosslinking between the polymers; (ii) at least one first macrocyclic ring which forms a pseudorotaxane with a polymer in the polymer network; and (iii) at least one second macrocyclic ring that does not form the pseudorotaxane. The hydrogel composition has a viscosity which allows for 3-D printing of the hydrogel to form a 3-D structure, and a storage (elastic) modulus after crosslinking that allows for the 3-D structure to undergo reversible 3-D structural deformation upon change of solvent conditions. Also provided are methods of manufacturing the compositions and 3-D structures.

29 Claims, 26 Drawing Sheets

Related U.S. Application Data division of application No. 15/814,201, filed on Nov. 15, 2017, now Pat. No. 10,954,315.

(51) Int. Cl.

| | |
|---|---|
| *A61L 15/22* | (2006.01) |
| *A61L 15/26* | (2006.01) |
| *A61L 15/28* | (2006.01) |
| *A61L 15/60* | (2006.01) |
| *A61L 26/00* | (2006.01) |
| *A61L 27/18* | (2006.01) |
| *A61L 27/20* | (2006.01) |
| *A61L 27/26* | (2006.01) |
| *A61L 27/52* | (2006.01) |
| *B33Y 10/00* | (2015.01) |
| *B33Y 70/00* | (2020.01) |
| *B33Y 80/00* | (2015.01) |
| *C08G 65/332* | (2006.01) |
| *C08G 83/00* | (2006.01) |
| *C08J 3/075* | (2006.01) |
| *C08J 3/24* | (2006.01) |
| *C08L 71/02* | (2006.01) |
| *A61K 9/00* | (2006.01) |
| *A61K 9/06* | (2006.01) |

(52) U.S. Cl.
CPC ............. *A61L 15/26* (2013.01); *A61L 15/28* (2013.01); *A61L 15/60* (2013.01); *A61L 26/0019* (2013.01); *A61L 26/0023* (2013.01); *A61L 26/008* (2013.01); *A61L 27/18* (2013.01); *A61L 27/20* (2013.01); *A61L 27/26* (2013.01); *A61L 27/52* (2013.01); *B33Y 10/00* (2014.12); *B33Y 70/00* (2014.12); *B33Y 80/00* (2014.12); *C08G 65/332* (2013.01); *C08G 83/007* (2013.01); *C08G 83/008* (2013.01); *C08J 3/075* (2013.01); *C08J 3/246* (2013.01); *C08L 71/02* (2013.01); *A61K 9/0024* (2013.01); *A61K 9/06* (2013.01); *C08G 2650/58* (2013.01); *C08J 2300/21* (2013.01); *C08J 2371/02* (2013.01); *C08L 2203/02* (2013.01)

(58) Field of Classification Search
CPC .. C08G 65/332; C08G 83/007; C08G 83/008; C08G 2650/58; C08J 3/075; C08J 3/246; C08J 2371/02; C08L 71/02; C08L 2203/02

See application file for complete search history.

(56) References Cited

PUBLICATIONS

Simoes, S.M.N. et al. Syringeable Pluronic-a-cyclodextrin supramolecular gels for sustained delivery of vancomycin. European Journal of Pharmaceutics and Biopharmaceutics 80 (2012) 103-112 (Year: 2012).*

Yuan, R. et al. Supramolecular Micellization and pH-Inducible Gelation of a Hydrophilic Block Copolymer by Block-specific Threading of a-Cyclodextrin. Journal of Polymer Science: Part B: Polymer Physics. vol. 46, 782-790 (2008) (Year: 2008).*

Zhao, S-P. Fabrication of Novel Supramolecular Hydrogels with High Mechanical Strength and Adjustable Thermosensitivity. J. Phys. Chem. B, 2006 vol. 110. 16503-16507 (Year: 2006).*

Pradal, C. Hydrolytically Degradable Polyrotaxane Hydrogels for Drug and Cell Delivery Applications. Biomacromolecules 2015, 16, 389-403 (Year: 2015).*

\* cited by examiner

| Polypseudorotaxane hydrogels | Molar ratio of EO/CD | Molar ratio of F127/CD | Storage modulus[a] [kPa] | Viscosity[b] [Pa] |
|---|---|---|---|---|
| PRH[5, 10] | 7.6:1 | 1:26.2 | 7.4 | 15 |
| PRH[5, 14.5] | 5.3:1 | 1:37.9 | 7.6 | 19 |
| PRH[5, 20] | 3.8:1 | 1:52.3 | 91.1 | 70 |
| PRH[7.5, 14.5] | 7.9:1 | 1:25.3 | 5.4 | 30 |
| PRH[10, 14.5] | 10.5:1 | 1:19.0 | 3.9 | 54 |

[a] Storage modulus values recorded in the linear viscoelastic plateau.
[b] Viscosity value at the shear rate of 1 s$^{-1}$.

FIG. 2

| PRHs | F127-MA$_2$ (w/v %) | α-CD (w/v %) | Molar ratio | |
|---|---|---|---|---|
| | | | EO/α-CD [a] | F127/ α-CD |
| PRH[5 [b], 10 [c]] | 5% | 10% | 7.6:1 | 1:26.2 |
| PRH[5, 14.5] | 5% | 14.5% [d] | 5.3:1 | 1:37.9 |
| PRH[5, 20] | 5% | 20% | 3.8:1 | 1:52.3 |
| PRH[5, 30] [e] | 5% | 30% | 2.5:1 | 1:78.5 |
| PRH[7.5, 14.5] | 7.5% | 14.5% [d] | 7.9:1 | 1:25.3 |
| PRH[7.5, 20] | 7.5% | 20% | 5.7:1 | 1:34.9 |
| PRH[7.5, 22] | 7.5% | 22% | 5.2:1 | 1:38.4 |
| PRH[7.5, 30] [e] | 7.5% | 30% | 3.8:1 | 1:52.3 |
| PRH[10, 14.5] | 10% | 14.5% [d] | 10.5:1 | 1:19.0 |
| PRH[10, 20] | 10% | 20% | 7.6:1 | 1:26.2 |
| PRH[10, 30] | 10% | 30% | 5.1:1 | 1:39.2 |
| PRH[10, 40] [e] | 10% | 40% | 3.8:1 | 1:52.3 |

[a] the molar number of the repeating unit ethylene oxide (EO) was calculated based on 200 EO units per F127-MA$_2$. [b] w/v % of F127-MA$_2$ in a PRH. [c] w/v % of α-CD in a PRH. [d] w/v % of the saturated aqueous α-CD solution at 25 °C. [e] a macroscopic phase separation was observed in these PRHs at room temperature.

FIG. 10

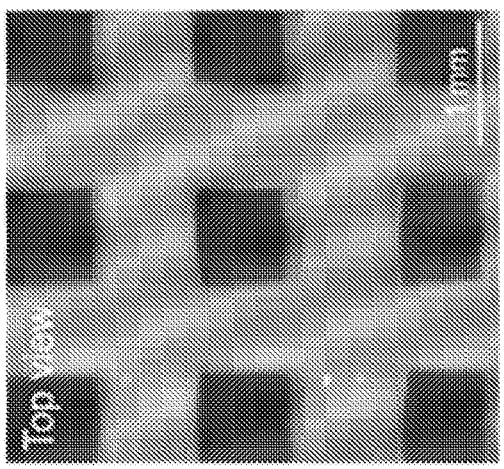
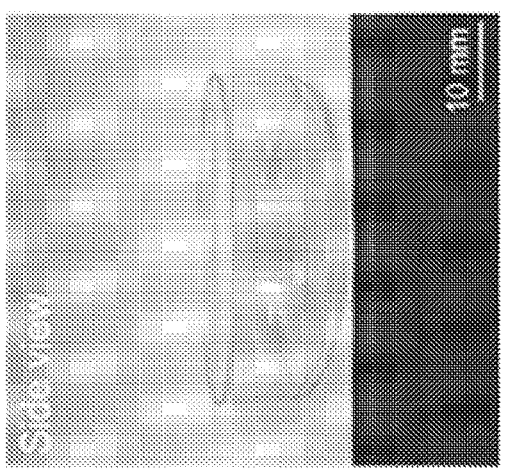
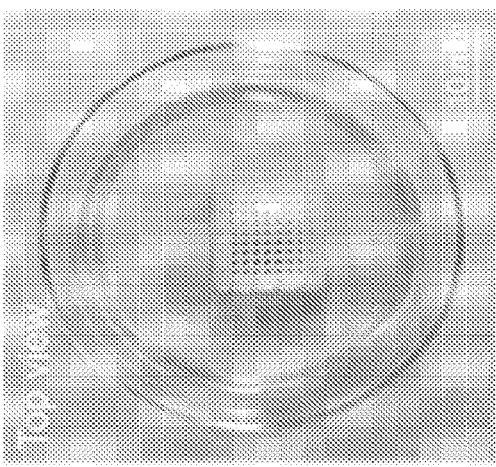
FIG. 15

| PM | Mass (g) | Solvent uptake ratio (mg/mg gel) | | MES.01 | Mass (g) | Solvent uptake ratio (mg/mg gel) |
|---|---|---|---|---|---|---|
| Dry gel | 0.0644 | 1 | | Dry gel | 0.0419 | 1 |
| DMSO-gel | 3.4833 | 54 | | DMSO-gel | 1.7424 | 41 |
| Hydrogel | 1.3212 | 21 | | Hydrogel | 1.915 | 45 |

FIG. 21

MECHANICALLY INTERLOCKED MOLECULES-BASED MATERIALS FOR 3-D PRINTING

CROSS-REFERENCE TO RELATED APPLICATIONS

This application is a continuation of U.S. Non-Provisional patent application Ser. No. 17/174,720, filed on Dec. 12, 2021, which is a divisional of U.S. Non-Provisional patent application Ser. No. 15/814,201, filed on Nov. 15, 2017. The entirety of each of the aforementioned applications is incorporated herein by reference.

BACKGROUND OF INVENTION

Amplification of molecular motions into the macroscopic world has great potential in the development of smart materials. Mechanically interlocked molecules (MIMs), including rotaxanes and polyrotaxanes, catenanes, and molecular knots, have been widely applied in the advancement of molecular shuttles, switches, muscles, and pumps, where light or chemical energy can be converted into molecular motions upon external stimuli.

While great strides have been made in recent years, it remains challenging to incorporate MIMs into bulk materials such that their molecular motions can be effectively and cohesively transformed into the macroscopic scale. The randomly oriented MIMs often counterbalance each other's mechanical work, thus affording no useful work macroscopically. Controlling the spatial assembly of MIMs and synchronizing their mechanical motions will amplify these molecular motions to a sizeable macroscopic event. Additive manufacturing (also commonly referred to as three-dimensional (3-D) printing may create physical objects, structures, articles, etc., based upon a computer-controlled program which instructs the 3-D printer how to deposit successive layers of extruded material which may be hardened by various methods.

It would thus be desirable to integrate mechanically interlocked molecules into complex 3-D architectures by direct-write 3-D printing, which would be capable of exhibiting macroscopic shape memory and/or is capable of converting chemical energy input into mechanical work by switching the motion of the α-cyclodextrin rings between random shuttling and stationary states.

SUMMARY OF THE INVENTION

The present disclosure is directed to methods of printing 3-D structures using polypseudorotaxane supramolecular hydrogels and the structures that result from them. These hydrogels are shear-thinning (which allows for their extrusion through needles) and rapidly self-healing, allowing disrupted bonds to form again. Developing functional materials by integrating polypseudorotaxane supramolecular hydrogels into a defined 3-D architecture allows for rapid and effective amplification of molecular motions into macroscopic scale events. Integrating additive manufacturing (3-D printing) with polypseudorotaxane supramolecular hydrogels allows for amplifying solution-based molecular motions to the macroscale by using 3-D geometries with complex internal structures including voids, such as woodpile lattices. By employing additional free macrocyclic rings, e.g., a cyclodextrin rings to facilitate the hydrogen-bonding network formed between the polypseudorotaxanes, resultant shear-thinning and self-healing properties allowed for printable polypseudorotaxane-based hydrogels (PRHs) for direct-write 3-D printing. Disrupting the hydrogen bonding network in, e.g., the tubular arrays of a cyclodextrin rings and crystalline domains of the inter-ring hydrogen bonding interactions, which allows the α cyclodextrin rings to shuttle dynamically along the axles of the polyrotaxanes, thus weakening the mechanical strength of monoliths formed therefrom, leading to 3-D structural deformation. Re-establishing the inter-ring hydrogen bonding reconstitutes the 3-D structure of the monolith. Thus, the molecular shuttling motions of the molecularly interlocked architectures into the macroscopic motion of the monolith through the conversion of chemical energy input into mechanical work.

In one embodiment, the present invention includes a supramolecular polypseudorotaxane hydrogel composition capable of reversible 3-D structural deformation. The composition may comprise (a) a solvent; (b) an at least partially linear polymer, where the polymer further comprises groups capable of covalent crosslinking between the polymers (e.g., polymer molecules); (ii) at least one first macrocyclic ring which forms a pseudorotaxane with a polymer in the polymer network; and (iii) at least one second macrocyclic ring that does not form the pseudorotaxane. In an embodiment, the hydrogel composition has a viscosity which allows for 3-D printing of the hydrogel to form a 3-D structure, and a storage (elastic) modulus after crosslinking that allows for the 3-D structure to undergo reversible 3-D structural deformation upon change of solvent conditions.

In one embodiment, the supramolecular polypseudorotaxane hydrogel composition's polymer network comprises an at least partially linear polymer, wherein the at least partially linear polymer is in an amount of from about 1 to about 20% w/v of the composition; and the at least one first and second macrocyclic ring are the same and are in an amount of from about 3 to about 30% w/v of the composition. In one embodiment, the composition is capable of maintaining the shape and dimensional stability in a 3-D pattern after 3-D printing and covalent crosslinking of the at least partially linear polymers.

In one embodiment, the reversible 3-D structural deformation upon change of solvent conditions is capable of allowing the composition to perform mechanical work.

In one embodiment, the at least one second macrocyclic ring is capable of participating in non-covalent bonding with at least first macrocyclic ring forming the polypseudorotaxane structure to form a reversible crystalline structure; or, wherein the at least one first macrocyclic ring forming the polypseudorotaxane structure participate in the reversible 3-D structural deformation by ring shuttling upon change of solvent conditions.

The at least partially linear polymer may be an amphiphilic or hydrophilic polymer, and may be ionic or nonionic. In one embodiment, the at least partially linear polymer is a nonionic amphiphilic polymer. The amphiphilic polymer may be present at a concentration either at, below or above its critical micellular concentration (cmc). Properties of the polymers and the polymer solution may be manipulated by adjusting the cmc, as is known in the art. In one embodiment, the polymer is used at above its cmc to allow for micellular formation. A nonionic amphiphilic polymer can include a copolymer comprising at least one block of lesser hydrophilicity and at least one hydrophilic block; optionally including at least one central block of lesser hydrophilicity and at least two terminal hydrophilic blocks. In embodiments, the at least partially linear polymer is a nonionic polymer wherein the hydrophilic blocks are selected from the group consisting of polyethylene oxide (PEO), polyethylene imide, and polyvinyl alcohol, and the block of lesser hydrophilicity (and/or hydrophobic block) is selected from the group consisting of polypropylene oxide (PPO), polydimethylsiloxane (PDMS), polystyrene, and polycaprolactone (PCL). In one embodiment, the nonionic amphiphilic polymer is a copolymer comprising poly(ethylene oxide) and poly(propylene oxide), or a PEO-PPO-PEO triblock copolymer; or a block copolymer with an approximate proportion of blocks of ($E_{21}P_{67}E_{21}$) and ($E_{98}P_{67}E_{98}$). The polymer may be biocompatible.

In an embodiment, the composition includes where the macrocyclic ring is a cyclodextrin or a modified cyclodextrin derivative, such as α-cyclodextrin, a β-cyclodextrin, or an γ-cyclodextrin, which may be optionally derivatized.

In one embodiment, the partially linear polymer is present in an amount of from about 1 to about 20% w/v of the composition and the macrocyclic ring capable of forming a pseudorotaxane is present in an amount of from about 5 to about 30% w/v of the composition. In embodiments, the composition may include wherein the at least partially linear polymer is a copolymer comprising poly(ethylene oxide) and poly(propylene oxide) and is present in an amount of about 5% w/v of the composition and the macrocyclic ring capable of forming a pseudorotaxane is a cyclodextrin and is present in an amount of from about 14.5 to about 25% w/v; 14.5 to about 20% w/v; 20 to about 25% w/v; or about 22% w/v of the composition. In some embodiments, at least partially linear polymer is a copolymer comprising poly (ethylene oxide) and poly(propylene oxide) and is present in an amount of from about 10% w/v of the composition and the macrocyclic ring capable of forming a pseudorotaxane is a cyclodextrin and is present in an amount of from about 20 to about 35% w/v, or about 30% w/v, of the composition In another embodiment, in the composition the molar ratio of the at least partially linear polymer to macrocyclic ring is about 30:1 to about 60:1; about 35:1 to about 55:1; or wherein the molar ratio of the hydrophilic repeating unit in the at least partially linear polymer to the macrocyclic ring is about 3:1 to about 6:1.

In embodiments, in the composition the storage modulus is at least about 0.5 to 500 kPa, and/or, in the composition the viscosity at a shear rate of 1 $s^{-1}$ and 25° C. is between 1 and 500 Pa·s.

In embodiments, the groups capable of covalent crosslinking between the polymers are groups capable of a free radical reaction or a condensation reaction. In one embodiment, the covalent crosslinking is a photo-initiated free radical reaction.

The composition may undergo a reversible 3-D structural deformation upon change of solvent conditions which may include solvent change or pH change.

The invention also includes a 3-D structure as described herein. Such structures may include a shaped implantable tissue graft scaffold, an implantable cellular matrix, a drug release reservoir, a model tissue, an implantable gel, a wound dressing, a sensing device, a pH sensor, a wearable device, or a sorption device.

The invention also includes a method of manufacturing a supramolecular polypseudorotaxane hydrogel composition capable of reversible 3-D structural deformation, which steps include (a) providing a solvent; (b) providing an at least partially linear polymer, wherein the at least partially linear polymer is in an amount of from about 1 to about 20% w/v of the composition, and wherein the polymer comprises groups capable of covalent crosslinking between at least partially linear polymers; and/or (c) providing at least one first macrocyclic ring which forms a pseudorotaxane in an amount of from about 10 to about 30% w/v of the composition; wherein the amount of the first macrocyclic ring is in excess of the amount to form the pseudorotaxane. In embodiments, the hydrogel composition has a viscosity which allows for 3-D printing of the hydrogel to form a 3-D structure, and a storage (elastic) modulus after crosslinking that allows for the 3-D structure to undergo reversible 3-D structural deformation upon change of solvent conditions. In embodiments, the groups capable of covalent crosslinking between the at least partially linear polymers is N-aminoethyl-methylacrylamide and the change of solvent conditions is a pH change.

In embodiments, the present invention also includes a method of manufacturing a three-dimensional structure comprising a polypseudorotaxane hydrogel composition of the invention. The method may include the steps of delivering one or more polypseudorotaxane hydrogel compositions onto a surface of a substrate to form the 3 dimensional structure, wherein the 3-D structure comprises internal cavities or voids that are interconnected in one, two or three dimensions within the structure; and providing conditions for polymerization. The method of delivering may include addition manufacturing or 3-D printing.

The present invention includes compositions and 3-D structures made by the methods of the invention.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

BRIEF DESCRIPTION OF THE DRAWINGS

FIG. 2. Molar ratios of repeating units EO and F127 to CD and viscoelastic parameters of the polypseudorotaxane hydrogels.

FIG. 10. Preparation of polypseudorotaxane hydrogels (PRHs) with various amounts of the axle (F127-MA$_2$) and ring (α-CD) precursors.

FIG. 15. Optical images of an as-printed PRH[5,20] woodpile lattice cube, x×y×z=12×12×5 mm, line width=600 μm.

FIG. 21. Solvent uptake analysis of PM and M[5,0].

DETAILED DESCRIPTION OF THE INVENTION

Figure 1:
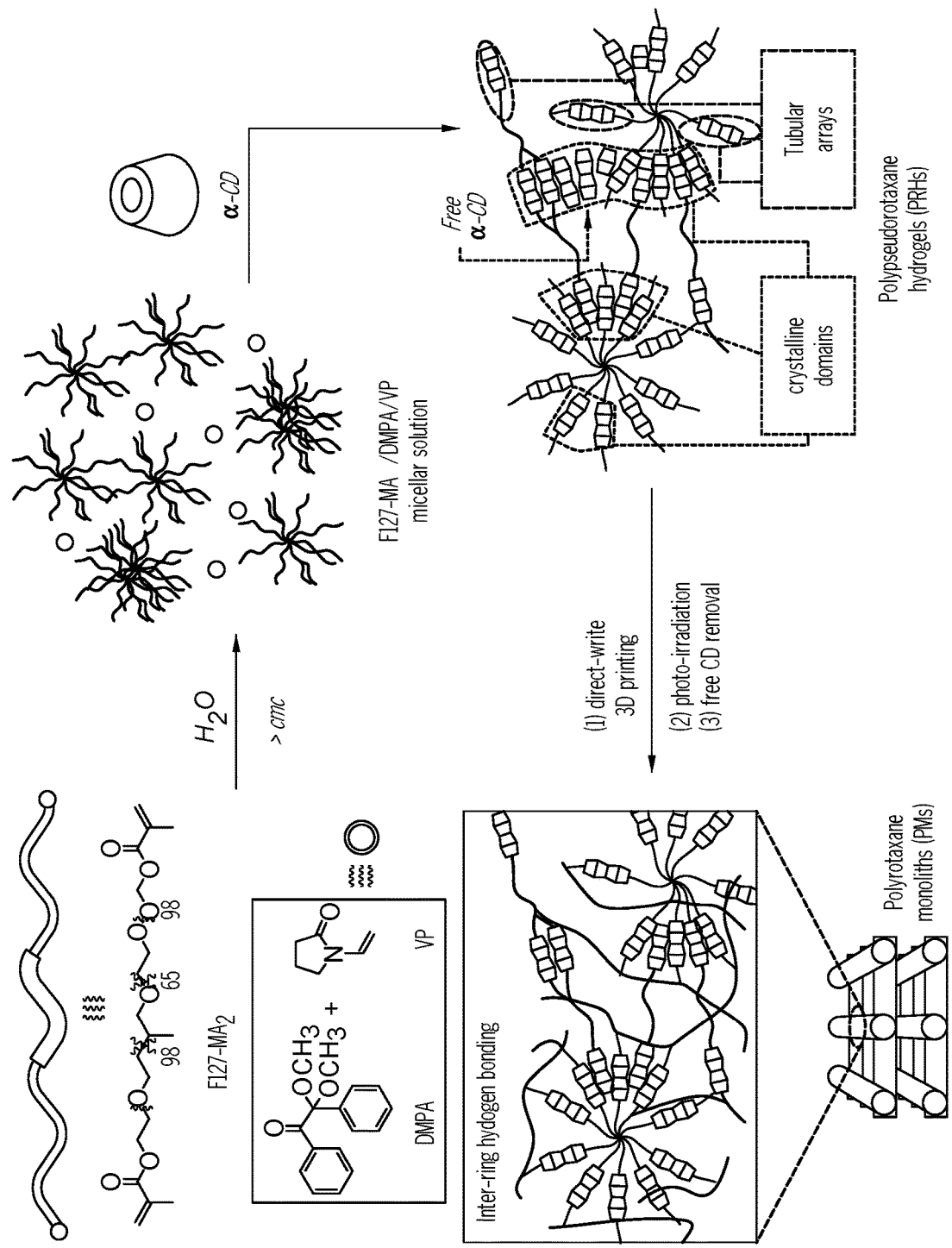
FIG. 1. Design and synthesis of 3-D printable polypseudorotaxane hydrogels and the fabrication of polyrotaxane monoliths using the direct-writing technique.

In general, the terms and phrases used herein have their art-recognized meaning, which can be found by reference to standard texts, journal references and contexts known to those skilled in the art. The following definitions are provided to clarify their specific use in the context of the invention.

Demonstrated here is an approach that integrates mechanically interlocked molecules into complex three-dimensional (3-D) architectures by direct-write 3-D printing. The design and synthesis of polypseudorotaxane hydrogels, which are composed of α-cyclodextrins and poly(ethylene oxide)-poly(propylene oxide)-poly(ethylene oxide) (PEO-PPO-PEO) triblock copolymers, and their subsequent fabrication into polyrotaxane-based lattice cubes by 3-D printing followed by post-printing polymerization are reported. By switching the motion of the α-cyclodextrin rings between random shuttling and stationary states through solvent exchange, the polyrotaxane monolith not only exhibits macroscopic shape-memory properties but is also capable of converting the chemical energy input into mechanical work by lifting objects against gravity.

In one embodiment, the present invention includes a supramolecular polypseudorotaxane hydrogel composition capable of reversible 3-D structural deformation.

The term rotaxane may be used to designate a mechanically interlocked molecular architecture consisting of a "dumbbell shaped molecule" which is threaded through a "macrocycle". The name is derived from the Latin for wheel (rota) and axle (axis). Polyrotaxanes are defined as molecular assemblies, in which many macrocycles are mechanically interlocked on a dumbbell-shaped molecule by bulky stoppers on its ends. The term pseudorotaxane may be used to designate any complex, having the general form of a rotaxane, but in which the linear or at least partially linear component does not have bulky end groups. A polypseudorotaxane are defined as molecular assemblies, in which many macrocycles are mechanically interlocked on a dumbbell-shaped molecule without bulky end groups. In the instant invention, to allow for ring-shuttling interactions, the present invention, in one embodiment, incorporates polypseudorotaxanes.

The term "gel", "hydrogel" and the like is intended to connote that meaning also normally associated with that term—i.e., a material comprising at least one solid matter that is stabilized by bonds giving it a 3-D structure, but whose molecular structure/network can be infiltrated by the molecules of a liquid, where such infiltration may or may not alter the shape or dimensions of the 3-D structure. As used herein, the term "(hydro)gel" is intended to connote that meaning also normally associated with that term—i.e., a three-dimensional hydrophilic network comprising hydrophilic polymers, in which water is the dispersion medium, and are capable of maintaining their structural integrity. (Hydro)gels are highly swollen (they can contain over 99.9% water) natural or synthetic polymers. (Hydro)gels also possess a degree of flexibility very similar to natural tissue, due to their significant water content. Supra-molecular gels or (hydro)gels are a specific class of materials, which are described elsewhere herein. As used herein, the term "(hydro)gel" is intended to connote separate embodiments where one embodiment is a gel and another embodiment is a (hydro)gel.

The composition may comprise (a) a solvent. The solvent, in one embodiment, may be a polar solvent generally having a larger dipole moment between atoms of different electronegativities. In one embodiment, the solvent will have a high dielectric constant (greater than 20) which allows the solvent to support e.g., hydrogen bonding with the solutes. The solvent may be a polar protic or polar aprotic solvent. In one embodiment, the polar protic solvent is useful for participating in hydrogen bonding in the polypseudorotaxane compositions of the invention. Polar protic solvents include aqueous solutions comprising water, as well as alcohols such as t-butanol, n-propanol, ethanol, methanol, acetic acid and combinations thereof. Polar aprotic solvents have large dielectric constants (greater than 20) and large dipole moments but do not participate in hydrogen bonding due to lack of O—H or N—H bonds. The high polarity of polar aprotic solvents allows for dissolution of charged species. Examples of polar aprotic solvents include acetone, N,N-dimethylformamide, acetonitrile, dimethyl sulfoxide.

The composition may comprise (b) an at least partially linear polymer, where the polymer further comprises groups capable of covalent crosslinking between the polymers.

As described above, the settable, shear-thinning (hydro) gels comprise a hydrophilic polymer network, comprising hydrophilic polymers or copolymers containing hydrophilic polymer subunits. These polymers may comprise natural, synthetic, biocompatible, biodegradable, non-biodegradable, and/or biosorbable building blocks. Unless specifically restricted to one or more of these categories, the polymers may comprise materials from any one of these categories.

For performance reasons, it may be desirable to incorporate biodegradable or porogenic materials into the design.

The term "polymer" is not intended to necessarily refer to a single polymer; rather it is intended to also connote a mixture of individual molecules, said mixture having a distribution of molecular weights, as is understood by those skilled in the art. The present invention is not limited to any particular molecule weight distribution, provided the distribution provides a mixture suitable for the purposes described herein. For example, a polymer comprising hyaluronic acid refers to a mixture of individual polymers, each molecule comprising hyaluronic acid.

The phrase "synthetic polymer" refers to polymers that are not found in nature, even if the polymers are made from naturally occurring biomaterials. Examples include, but are not limited to, poly(amino acids), copoly(ether-esters), polyalkylenes, oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, polysiloxanes, and combinations thereof The phrase "biocompatible polymer" refers to any polymer (synthetic or natural) which when in contact with cells, tissues or body or physiological fluid of an organism does not induce adverse effects such as immunological reactions and/or rejections and the like. It will be appreciated that a biocompatible polymer can also be a biodegradable polymer.

In some embodiments, the at least partially linear polymer functions as the "axle" molecule of the polypseudorotaxane hydrogel compositions of the present invention. These "axle" polymers can be any at least partially linear compounds. The linear axle molecule can be a long-chain carbon molecule, optionally substituted with nitrogen atoms or oxygen atoms. In some embodiments, the linear axle molecule can be a polymer.

The at least partially linear polymer may be an amphiphilic or hydrophilic polymer, and may be ionic or nonionic. In one embodiment, the at least partially linear polymer is a nonionic amphiphilic polymer. The amphiphilic polymer may be present at a concentration either at, below or above its critical micellular concentration (cmc). In one embodiment, the polymer is used at above its cmc to allow for micellular formation in the polypseudorotaxane compositions of the invention.

The polymer can be a homopolymer. In some embodiments, a "homopolymer" is a polymer where only one type of monomers is used. Examples of homopolymers include, but are not limited to, polyvinyl alcohol, poly(meth)acrylic acid, polyacrylamide, poly(ethylene oxide), poly(propylene oxide), poly(ethylene glycol), polyisoprene, poly(propylene glycol), poly(vinyl methyl ether), polyethylene, polypropylene, polyisobutylene, polybutadiene, polyureas, polysulfides, polydimethylsiloxane. In some embodiments, the linear molecule may be selected from the group consisting of poly(ethylene glycol), poly(propylene glycol), polydimethylsiloxane, polyethylene, and polypropylene.

In some embodiments, the at least partially linear axle molecule can be a copolymer. A "copolymer" can be called a "heteropolymer." In some embodiments, a copolymer refers to a polymer derived from two or more monomeric species. It can be a block copolymer, which includes two or more chemically distinct homopolymer blocks linked by covalent bonds. The block copolymer can be a diblock copolymer, a triblock copolymer, or a block copolymer with more than three distinct blocks. For example, it can be poly(ethylene glycol)-poly(propylene glycol)-poly(ethylene glycol) triblock copolymer. Poloxamers (PLURONICS) are another triblock copolymer which is composed of a central chain of poly(propylene oxide) (PPO) flanked by two chains of poly(ethylene oxide) (PEO).

In embodiments, the at least partially linear polymer is a nonionic polymer wherein the hydrophilic blocks are selected from the group consisting of polyethylene oxide (PEO), polyethylene imide, and polyvinyl alcohol, and the block of lesser hydrophilicity (and/or the hydrophobic block) is selected from the group consisting of polypropylene oxide (PPO), polydimethylsiloxane (PDMS), polystyrene, and polycaprolactone (PCL). In one embodiment, the nonionic amphiphilic polymer is a copolymer comprising poly(ethylene oxide) and poly(propylene oxide), or a PEO-PPO-PEO triblock copolymer; or a block copolymer with an approximate proportion of blocks of $(E_{21}P_{67}E_{21})$ and $(E_{98}P_{67}E_{98})$. Mixtures of polymers such as guest/host polymers may also be used.

In some embodiments, the average molecular weight of the linear molecule, such as a polymer, may range from about 1 kDa to about 80 kDa, or from about 1 kDa to about 60 kDa, or from about 5 kDa to about 80 kDa, or from about 5 kDa to about 60 kDa. In some embodiments, the average molecular weight of the polymer can be from about 1 kDa to about 40 kDa, or from about 1 kDa to about 30 kDa, or from about 5 kDa to about 40 kDa, or from about 5 kDa to about 30 kDa, or from about 5 kDa to about 20 kDa. In some embodiments, the average molecular weight of the polymer may also range from about 1 kDa to about 10 kDa. In other embodiments, the average molecular weight of the polymer may range from about 20 kDa to about 30 kDa. In some embodiments, the "average molecular weight" can refer to the weight average molecular weight (Mw), methods to derive the same are known in the art.

The molecules of the invention are pseudorotaxanes, i.e., lacking bulky groups which act to prevent dethreading of the macrocyclic rings from the polymer "axle" molecules. As such, polymerization of the polymers in the pseudorotaxane hydrogel compositions after formation of a structure following e.g., direct-writing or printing affords polypseudorotaxane monoliths with structural integrity.

With the respect to the chemical moieties capable of chemical covalent crosslinking, the term "at least one set" refers to the fact that the chemical moieties are the same or different chemical groups which react together to form a cross-link; i.e., from this perspective, the "at least one set" may be envisioned as comprising a matched pair of chemical groups. For example, a set may comprise a carboxylic acid (or equivalent) and an amine or alcohol (or equivalent), together capable of forming an amide or ester cross-linked linkage. In another example, a set may comprise a thiol group and a vinyl group, together capable of forming a thiol ether on reaction with light. Another set may comprise a hydrazide and an aldehyde or ketone, capable of forming a hydrazone. Or a set may comprise simply a single radical polymerizable moiety, such as an acrylate or methacrylate. In some embodiments, the polymer is methacrylated by methods known in the art.

These at least one set of chemical covalent cross-linkable moieties may be attached as a pendant to at least one polymer of the network, either directly to the polymer backbone or via a linking group. In other embodiments, the chemical covalent cross-linkable moieties may be embedded within the polymer backbone of at least one polymer of the network. Olefin or epoxy moieties may be examples of this strategy.

In certain embodiments, where the chemical moieties capable of chemical covalent crosslinking are activated, or "triggered" by exposure to external stimulus, such as radiation in the microwave range (i.e., in the range of about 1 MHz to about 10 GHz). In still other embodiments, the external stimulus may be a change in pH or temperature, a free radical initiator, or a combination thereof. Where the chemical covalent cross-linking reaction is a free radical polymerization, the (hydro)gel may further comprise a thermal radical initiator. Exemplary free radical initiators include azobisisobutyronitrile, dilauroyl peroxide lauroyl acid, dioctanoyl peroxide caprylic acid, didecanoyl peroxide n-decanoic acid, di-n-propionyl peroxide propionic acid, bis(3,5,5-trimethylhexanoyl) 3,5,5-trimethyl peroxide hexanoic acid, dibenzoyl peroxide benzoic acid, bis(2,4-dichlorobenzoyl) 2,4 dichlorobenzoic acid peroxide, bis(o-methylbenzoyl) peroxide o-methyl benzoic acid, acetyl cyclohexane sulphonyl cyclohexane sulphonic peroxide acid, t-butylperoxypivalate pivalic acid, t-butyl peroxy-2-ethylhexanoate 2-ethyl caproic acid, t-butyl peroxy isobutyrate isobutyric acid, t-butyl peroxybenzoate benzoic acid, and mixtures thereof In certain embodiments, the covalent crosslinking reaction is a condensation reaction or a free radical polymerization reaction. In related embodiments, the at least one set of chemical moieties capable of participating in a covalent chemical crosslinking reaction comprises an acrylate, acrylamide, optionally protected alcohol, aldehyde, alkyne, optionally protected amine, anhydride, azide, carboxy, epoxy, ester, hydrazide, ketone, maleimide, methacrylate, styrenyl, optionally protected thiol, or vinyl or vinyl sulfone group. In still further related embodiments, the product of the chemical covalent cross-linking reaction is an ester, ether, amide, hydrozone, polyacrylate, polymethacrylate, thioamide, thioester, thioether, or urethane.

In embodiments, 2,2-dimethoxy-2-phenylacetophenone (DMPA) and N-vinylpyrrolidone (VP) are employed as a photoinitiator and solubilizing agent for the crosslinking reaction. This skilled artisan would appreciate how to modify the desired polymer to attached or incorporate, the chemical covalent cross-linkable moiety.

The compositions of the invention also include (ii) at least one first macrocyclic ring which forms a pseudorotaxane with a polymer in the polymer network; and (iii) at least one second macrocyclic ring that does not form the pseudorotaxane. The first and second macrocyclic rings may be the same or different. In some embodiments, a "macrocyclic molecule" or "macrocyclic ring" can be a cyclic macromolecule or a macromolecular cyclic portion of a molecule. In other embodiments, a macrocyclic molecule can also refer to a macrocyclic compound. The macrocyclic molecule can be a porphyrin or an analog or derivative thereof. The macrocyclic molecule can be a polyether macrocycle, an analog or derivative, or a combination thereof, for example, a crown ether (e.g., benzo[24]crown-8). The macrocyclic molecule can be an analog or derivative or a combination thereof. The macrocyclic molecule can be a cyclic oligosaccharide, for example, cyclodextrin (CD). In some embodiments, the "cyclodextrin" can be composed of glucose monomers coupled together to form a conical, hollow molecule with a cavity. The cyclodextrin in the present invention can be any suitable cyclodextrins, including α-, β-, and γ-cyclodextrins, and their combinations, analogs, and derivatives. The cyclodextrin can be either natural or modified, for example, modified with a chelating agent moiety, or derivatized.

In an embodiment, the hydrogel composition has a viscosity (shear-thinning) which allows for 3-D printing of the hydrogel to form a 3-D structure, and a storage (elastic) modulus after crosslinking that allows for the 3-D structure to undergo reversible 3-D structural deformation upon change of solvent conditions. These properties are critical to define as the major challenge associated with developing polypseudorotaxane-based inks for direct writing is to tailor their rheological properties to allow for flow through the nozzle during the direct writing process (shear-thinning) and rapidly recover their mechanical strength afterward (self-healing).

In the present context, the term shear thinning has a meaning normally associated with that term—i.e., an effect where a fluid's viscosity (the measure of a fluid's resistance to flow) decreases with an increasing rate of shear stress. As contemplated herein, such shear-thinning (hydro)gels are composed of two or more polymers or oligomers that are held together in unique structural relationships by forces other than those of full covalent bonds, e.g., hydrogen bonds. Non-covalent bonding is critical in the described shear-thinning and self-healing properties.

The polypseudorotaxane compositions of the invention are preferably shear-thinning (which allows for their extrusion through needles) and rapidly self-healing (which allows the disrupted bonds to form again). Depending on the supramolecular chemistry used, properties of these materials can also be tuned, including mechanical/rheological properties and dynamic properties such as kinetics of bond formation. While supramolecular (hydro)gels are preferred embodiments, the present disclosure is not limited to these embodiments and other classes of materials, for example sol-gels and colloidal suspensions, may also be employed.

In some embodiments, the supramolecular materials may serve as the printed "ink", the template material that receives printed material, or both. In some embodiments, the supramolecular bonding in an ink material enables a solid or (hydro)gel to be pushed through a channel, as in extrusion from a needle, as the driving stimulus of applied force causes bond dissociation that allows the material to behave in a fluid-like fashion. After the force is removed (for example, once the material leaves the needle and there are no tensile or compressive forces acting on the ink) bonds reform to stabilize the structure. Because the bonds dissociate during the application of force, a print head (e.g. needle) can be moved through the material, depositing an ink, which is then enclosed in the (hydro)gel as bonds reform. Any breaks in the material left by the needle will be healed by bonds that reform.

For each mechanism, the chemical covalent crosslinking results in a covalently cross-linked (hydro)gel having a mechanical stability that is higher than the mechanical stability of the shear-thinning (hydro)gel before chemical cross-linking. In separate embodiments, this "higher" mechanical stability may be described in terms of improved resistance to bio-erosion—defined in terms of disassociation of the non-covalent linkages; i.e., improved resistance correlating with longer times necessary to realize degradation of the polymer network—or increased viscosity, stiffness or higher storage or loss modulus of the polymer network. Within each of these property classes, this higher stability reflects an improvement or increase in at least one physical property of at least about 10%, at least about 25%, at least about 50%, or at least about 100%, or at least about 2 times, at least about 5 times, or at least about 10 times relative to the corresponding property of the shear-thinning (hydro)gel.

In additional to the settable, shear thinning (hydro)gels (i.e., which exists before the covalent crosslinking reaction(s) has occurred or is complete), individual embodiments of the present disclosure include those (hydro)gel compositions, based on the previous descriptions, which have undergone at least one of the covalent cross-linking reactions, either partially or completely. This includes embodiments where any number of the at least one set of the chemical moieties capable of covalent crosslinking of settable, shear thinning (hydro)gel has reacted, either partially or entirely.

In separate embodiments, the cured (hydro)gels exhibit a higher stability or lower diffusivity than the pre-cured (i.e., settable, shear thinning) (hydro)gel. In several of these embodiments, the cured, covalently cross-linked (hydro)gel exhibits a mechanical stability that is higher than the mechanical stability of the (pre-cured) shear-thinning (hydro)gel (i.e., before covalent crosslinking). In separate embodiments, this "higher" mechanical stability may be described in terms of improved resistance to bio-erosion—defined in terms of disassociation of the non-covalent linkages; i.e., improved resistance correlating with longer times necessary to realize degradation of the polymer network—or increased viscosity, stiffness or higher storage or loss modulus of the polymer network. Within each of these property classes, this higher stability reflects an improvement or increase in at least one physical property of at least about 10%, at least about 25%, at least about 50%, or at least about 100%, or at least about 2 times, at least about 5 times, or at least about 10 times, relative to the corresponding property of the shear-thinning (hydro)gel.

One challenge associated with developing polypseudorotaxane-based inks for direct writing is to tailor their rheological properties to allow for flow through the nozzle during the direct writing process and rapidly recover their mechanical strength afterward. Although the preparation and rheological properties of some PRHs have been investigated, these materials were not suitable for 3-D printing. For example, the present inventors, without being bound by theory, have determined that a densely crosslinking hydrogel formed by photo-crosslinking of a high concentration of polymer will be too rigid and overpower any polyrotaxane molecular behaviors at a macroscopic scale. In addition, previous to the instant invention, the self-healing properties are not understood.

Accordingly, the present inventors have determined ratios of the at least partially linear polymer and the macrocycle which will result in "inks" for direct writing and addition manufacturing, which are capable of reversible 3-D deformation. In one embodiment, the reversible 3-D structural deformation upon change of solvent conditions is capable of allowing the composition to perform mechanical work.

In one embodiment, the at least one second macrocyclic ring is capable of participating in non-covalent bonding with at least first macrocyclic ring forming the polypseudorotaxane structure to form a reversible crystalline structure; or, wherein the at least one first macrocyclic ring forming the polypseudorotaxane structure participate in the reversible 3-D structural deformation by ring shuttling upon change of solvent conditions.

In one embodiment, the supramolecular polypseudorotaxane hydrogel composition's polymer network comprises an at least partially linear polymer, wherein the at least partially polymer is in an amount of from about 1 to about 20% w/v of the composition; and the at least one first and second macrocyclic ring are the same and are in an amount of from about 3 to about 30% w/v of the composition. In one embodiment, the composition is capable of maintaining the shape and dimensional stability in a 3-D pattern after 3-D printing and covalent crosslinking of the at least partially linear polymers.

In one embodiment, the partially linear polymer is present in an amount of from about 5 to about 10% w/v of the composition and the macrocyclic ring capable of forming a pseudorotaxane is present in an amount of from about 10 to about 30% w/v of the composition. The inventor has found that having a high α-cyclodextrin threading ratio compared to the axle is an important aspect of the self-healing properties of the instant invention.

In embodiments, the composition may include wherein the at least partially linear polymer is a copolymer comprising poly(ethylene oxide) and poly(propylene oxide) and is present in an amount of about 5% w/v of the composition and the macrocyclic ring capable of forming a pseudorotaxane is a cyclodextrin and is present in an amount of from about 14.5 to about 25% w/v; 14.5 to about 20% w/v; 20 to about 25% w/v; or about 22% w/v of the composition. In some embodiments, at least partially linear polymer is a copolymer comprising poly(ethylene oxide) and poly(propylene oxide) and is present in an amount of from about 10% w/v of the composition and the macrocyclic ring capable of forming a pseudorotaxane is a cyclodextrin and is present in an amount of from about 20 to about 35% w/v, or about 30% w/v, of the composition. In some embodiments, the partially linear polymer is a copolymer comprising poly(ethylene oxide) and poly(propylene oxide) is present in an amount of 5% w/v and the α-cyclodextrin is present in an amount of 20%; or the partially linear polymer is a copolymer comprising poly(ethylene oxide) and poly(propylene oxide) is present in an amount of 7.5% w/v and the α-cyclodextrin is present in an amount of 22%; or the partially linear polymer is a copolymer comprising poly(ethylene oxide) and poly(propylene oxide) is present in an amount of 10% w/v and the α-cyclodextrin is present in an amount of 30%.

Without being bound by theory, the inventors show that at FIG. 10, PRH [5,20], PRH[7.5,22] and PRH[10,30] were able to effectively self-heal within 15 seconds (the numbers within the brackets represent the concentration of F127-$MA_2$ and α-CD in % w/v, respectively). The inventors have found that reducing the concentration of the axle precursor F127-$MA_2$ did not result in decreased elastic and loss moduli of the obtained PRHs. Instead, the inventors showed that it is the increase in the concentration of α-CD from 10% to 20% w/v that caused the storage moduli G' to increase 12 times, indicating that the formation of pseudorotaxanes with their concomitant hydrogen bonding activity greatly improves the viscoelastic properties of the PRHs. The inventors found that the formation of microcrystalline domains between the polypseudorotaxanes act as supramolecular crosslinkers, which further strengthens the hydrogels. Studies show that the kinetics of the self-healing properties are critical for successful direct writing. Without being bound by theory, it is believed, based on rheological studies, that the rapid self-healing shown for PRHs with higher relative amounts of α-cyclodextrin (macrocyclic ring) to F127-$MA_2$ (at least partially linear polymer) is attributed to (1) high α-cyclodextrin threading ratio in the formed polypseudorotaxanes and (2) an accelerated microcrystalline domain reformation which is facilitated by unthreaded α-cyclodextrin, both of which promote the rapid re-establishment of hydrogen-bonding networks. Embodiments of the instant invention comprising even higher amounts of α-CD, such as e.g. PRH[5,30] and PRH[7.5, 30] and PRH[10, 40] as described herein, also participate in crystallization of polypseudorotaxanes and allow the compositions to achieve rapid self-healing capacity.

The ratios found for PRHs where the partially linear polymer is a copolymer comprising poly(ethylene oxide) and poly(propylene oxide) and α-cyclodextrin can be extrapolated to other at least partially linear polymers and to other macrocyclic rings by one of skill in the art using the guidance provided by the present invention. For example, effective PRHs of the invention include those having an overall molar ratio of the macrocyclic ring to at least partially linear polymer of greater than about 30:1 to about 60:1; greater than about 35:1 to about 55:1. Also for example, the molar number ratio of the hydrophilic repeating unit in the at least partially linear polymer to the macrocyclic ring is about 6:1 or less, about 6.5:1 or less, about 5:1 or less, about 4.5:1 or less, about 4:1 or less, or between about 6:1 to 2:1. From this guidance, appropriate ratios of other polymers of e.g., different block structures and/or different block ratios, different hydrophilicities, and the like to macrocyclic rings to form PRHs having the claimed properties can be determined.

For PRHs of the invention, in the composition the storage modulus may be at least about 0.5 to 500 kPa, and/or, in the composition the viscosity at a shear rate of 1 $s^1$ and 25° C. is between 1 and 500 Pa·s. Alternatively, the storage modulus can be between about 10 and 400 kPa, between about 20 and 300 kPa, between about 30 and 250 kPa, between about 40 and about 200 kPa, between about 50 and about 150 kPa, between about 60 and 120 kPa, between about 80 and 100 kPa. Alternatively, the viscosity at a shear rate of 1 $s^{-1}$ and 25° C. is between 1 and 500 Pa·s is between 10 and 400 Pa·s, between about 20 and 300 Pa·s, between about 30 and 250 Pa·s, between about 40 and about 200 Pa·s, between about 50 and about 150 Pa·s, between about 60 and 120 Pa·s, between about 80 and 100 Pa·s.

The composition, in embodiments, may undergo a reversible 3-D structural deformation upon change of solvent conditions which may include solvent change or pH change. As discussed elsewhere herein, hydrogen bonding formation and disruption may cause ring-shuttling motions which can disrupt macroscopic scale upon a change of solvent condition. Additionally, microcrystalline regions formed through hydrogen bonding may also be disrupted, also contributing to disruption of macroscopic scale. In one embodiment, this disruption is reversible.

In one embodiment, the hydrogen bonding is disrupted by changing from a polar protic solvent (such as aqueous solvent) to a polar aprotic solvent such as DMSO. Due to lack of groups to participate in hydrogen bonding, the polar aprotic solvent dismantles the macrocyclic ring hydrogen bonding interactions and deforms to lose strength and structure. In some embodiments, replacing DMSO with water changed the macroscopic rings from the random shuttling state to the hydrogen bonded stationary state and allowed the object (monolith) to quickly recover (within 2 min, within 4 min, within 6 min, within 8 min, within 10 min, within 15 min, within 20 min, within 30 min or within 60 min) its 3 D shape, or a shape within 50% of the original dimensions, within 40% of the original dimensions, within 35% of the original dimensions, within 30% of the original dimensions, within 25% of the original dimensions, within 20% of the original dimensions, within 15% of the original dimensions, within 10% of the original dimensions, or within 5% of the original dimensions. In some embodiments, the microcrystallization of the free macrocyclic rings will take longer, for example, between about 30 minutes and 10 hours, or between about 2 hours and 4 hours.

The reversible 3-D structural deformation may also be provided by pH change. For example, a structure formed by the present invention may be rendered pH responsive. The primary hydroxyl groups of α-CD are deprotonated above pH 11. When a 3-D-printed PM is soaked in water, simply increasing the environment pH>11 disrupts the primary face inter-ring interaction, forming ring dimers that shuttle along the polymer backbone. Since the F127-$MA_2$ that was employed in our preliminary studies hydrolyzes under the desired pH range, PEO-$AMA_2$ may be used as the polymer backbone and the pH dependent rheology e.g. elastic moduli in response to pH increase determined.

The invention also includes a 3-D structure comprising a supramolecular polypseudorotaxane composition, which includes (i) a crosslinked polymer network; (ii) at least one macrocyclic ring forming a pseudorotaxane with the crosslinked polymer network; and (iii) at least one second macrocyclic ring that does not form the pseudorotaxane. The macrocyclic ring molecules participate in non-covalent bonding with the first at least one macrocyclic ring forming a reversible crystalline structure; and the 3-D structure may have internal cavities or voids that are interconnected in one, two or three dimensions within the structure. Such structures may include a shaped implantable tissue graft scaffold, an implantable cellular matrix, a drug release reservoir, a model tissue, an implantable gel, a wound dressing, a pH sensor, a wearable device, or a sorption device.

The invention also includes a method of manufacturing a supramolecular polypseudorotaxane hydrogel composition capable of reversible 3-D structural deformation, which steps include (a) providing a solvent; (b) providing a at least partially linear polymer, wherein the at least partially linear polymer is in an amount of from about 5 to about 20% w/v of the composition, and wherein the polymer comprises groups capable of covalent crosslinking between at least partially linear polymers; and/or (c) providing at least one first macrocyclic ring which forms a pseudorotaxane in an amount of from about 10 to about 30% w/v of the composition; wherein the amount of the first macrocyclic ring is in excess of the amount to form the pseudorotaxane. In embodiments, the hydrogel composition has a viscosity which allows for 3-D printing of the hydrogel to form a 3-D structure, and a storage (elastic) modulus after crosslinking that allows for the 3-D structure to undergo reversible 3-D structural deformation upon change of solvent conditions. In embodiments, the groups capable of covalent crosslinking between the at least partially linear polymers is N-aminoethyl-methylacrylamide and the change of solvent conditions is a pH change.

The respective ink materials may be delivered by any suitable means, but in preferred embodiments, at least one of the ink materials is delivered by injection into or through the respective volume of the preceding ink or template material. Such injection may be accomplished by using a needle, cannula, catheter, or other tubing. It should be apparent that, in such cases, the dimensions of the internal volumes of the ink material(s) is defined by the internal dimensions of the injection devices used. As devices ranging from nanotube cellular probes through standard micron or millimeter dimensioned needles or other such devices are known, and can be used by these inventive methods, these internal structures may be defined as having at least one cross-sectional dimension (typically the diameter of a channel) in a range of from about 100 nm to about 500 nm, from about 500 nm to about 1000 nm, from about 1 micron to about 5 microns, from about 5 microns to about 10 microns, from about 10 microns to about 50 microns, from about 50 microns to about 100 microns, from about 100 microns to about 500 microns, from about 500 microns to about 1000 microns, from about 1 millimeter to about 5 millimeters, from about 5 millimeters to about 10 millimeters, or larger, or any combination of two or more of these ranges. Note also that, depending on the nature of the specific ink materials used, their further processing (for example, polymerization or crosslinking as described below) may result in expansion or contraction of the initially injected volumes, which may need to be considered in defining the ultimately desired dimensions. While the delivery devices typically have circular or ovoid cross-sections, devices with other cross-sectional shapes (e.g., triangles, squares. or other polygonal shapes, stars, etc.) can be employed to derive correspondingly shaped channels or tunnels.

Similarly, the lengths of internal channels or dimensions of internal voids can be any of the dimensions described above, as these are defined by the size of the original templates, which can be on the order of from about 100 nm to 1000 nm, from about 1 micron to about 1000 microns, from about 1 mm to about 10 mm, 100 mm, 1000 mm, or even larger. The templates can also be shape molded prior to providing (injecting) the ink materials, thereby providing articles nearly shape fit for their ultimate use, even before introduction of the inks, or subsequent selective removal techniques.

The flexibility of the present disclosure is further developed by the ability to incorporate materials or devices within any one or more of the inks or any portion of the template material. For example, in certain embodiments, any one of the at least one of the ink materials, the template material, or any combination thereof, may independently comprise pharmaceutically active drugs or nutraceuticals; populations of cells (including mammalian stem cells and progenitor cells); peptides or peptide derivatives; one or more types of nanoparticles (carbon, metallic, semiconductor, or inorganic oxide, carbide, or nitride) or quantum dots; conductive fillers (such as nanoscale carbon or metals), fluorescent or phosphorescent materials; magnetic materials; or combination thereof. Any one or more of these materials may also comprise a functional electronic device, such that the resulting structure forms an electrical or sensing connection to such a device. Similarly, the template material may be positioned adjacent to an electronic substrate material, comprising such a device, such that later formed channels or tunnels have access to devices capable of acting as chemical sensors or other electronic components.

In one set of embodiments, these additional materials comprise at least one therapeutic compound or agent, capable of modifying cellular activity. Similarly, agents that act to increase cell attachment, cell spreading, cell proliferation, cell differentiation and/or cell migration in the scaffold may also be incorporated into the (hydro)gels. Such agents can be biological agents such as an amino acid, peptides, polypeptides, proteins, DNA, RNA, lipids and/or proteoglycans. These agents may also include growth factors, cytokines, proteases, and protease substrates. Additionally and/or alternatively, the (hydro)gels of the present disclosure may comprise an antiproliferative agent, an immunosuppressant drug, and/or a non-thrombogenic or anti-adhesive substance. The cells which can be used according to the teachings of the present disclosure may comprise non-autologous cells or non-autologous cells (e.g. allogeneic cells or xenogeneic cells), such as from human cadavers, human donors or xenogeneic (e.g. porcine or bovine) donors. The cells may comprise a heterogeneous population of cells or a homogeneous population of cells. Such cells can be for example, stem cells, progenitor cells, or differentiated cells. Stem cells may include adipose derived stem cells, embryonic stem cells, bone marrow stem cells, cord blood stem cells, mesenchymal stem cells, adult stem cells, and pluripotent or induced pluripotent stem cells. Mesenchymal stem cells are preferred. Furthermore, such cells may be live or non-viable and/or of autologous origin or non-autologous origin, such as postpartum-derived cells. Typically the cells are selected according to the tissue being generated.

In additional to the settable, shear thinning (hydro)gels (i.e., which exists before the covalent crosslinking reaction(s) has occurred or is complete), individual embodiments of the present disclosure include those (hydro)gel compositions, based on the previous descriptions, which have undergone at least one of the covalent cross-linking reactions, either partially or completely. This includes embodiments where any number of the at least one set of the chemical moieties capable of covalent crosslinking of settable, shear thinning (hydro)gel has reacted, either partially or entirely.

In separate embodiments, the cured (hydro)gels exhibit a higher stability or lower diffusivity than the pre-cured (i.e., settable, shear thinning) (hydro)gel. In several of these embodiments, the cured, covalently cross-linked (hydro)gel exhibits a mechanical stability that is higher than the mechanical stability of the (pre-cured) shear-thinning (hydro)gel (i.e., before covalent crosslinking).

In some embodiments, further elaborated below, at least one, and preferably all, of the ink materials, the template materials, or additives thereof are biocompatible. In some cases, at least one, and preferably all, of the ink materials, the template materials, or additives thereof are suitable for implanting into a mammal, preferably a human.

The invention also includes a structure/composition as claimed or a composition/structure prepared by any of the methods described herein whether as an intermediate or final structure or device. Such exemplary non-limiting structures may provide the basis for, or be incorporated into, such devices as blood analyzers, micro-/nano-fluidic conduction or mixing devices, macro-, micro-, or nano-scale reaction vessels, artificial/replacement tissue scaffolds, tissue models, pumps, balloons, sensors (e.g., for toxins/pathogens, biomarkers), filters, and cell culture platforms. In other embodiments, the exemplary non-limiting structures may provide the bases for, or be incorporated into, such devices as shaped implantable tissue graft scaffolds, implantable cellular matrices, drug release reservoirs, model tissues, implantable (hydro)gels, including those for filling/bulking spaces energy storage devices, wound dressings, and sorption devices. Such devices are considered within the scope of the present disclosure.

In embodiments, the present invention also includes a method of manufacturing a three-dimensional structure comprising a polypseudorotaxane hydrogel composition of the invention. The method may include the steps of delivering one or more polypseudorotaxane hydrogel compositions onto a surface of a substrate to form the 3 dimensional structure, wherein the 3-D structure comprises internal cavities or voids that are interconnected in one, two or three dimensions within the structure; and providing conditions for polymerization. The method of delivering may include addition manufacturing or 3-D printing.

The present invention includes compositions and 3-D structures made by the methods of the invention.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

Example 1: Ring Shuttling Controls Macroscopic Motion in a Three-Dimensional Printed Polyrotaxane Monolith Abstract Amplification of molecular motions into the macroscopic world has great potential in the development of smart materials. Demonstrated here is an approach that integrates mechanically interlocked molecules into complex three-dimensional (3-D) architectures by direct-write 3-D printing. The design and synthesis of polypseudorotaxane hydrogels, which are composed of α-cyclodextrins and poly (ethylene oxide)-poly(propylene oxide)-poly(ethylene oxide) (PEO-PPO-PEO) triblock copolymers, and their subsequent fabrication into polyrotaxane-based lattice cubes by 3-D printing followed by post-printing polymerization are reported. By switching the motion of the α-cyclodextrin rings between random shuttling and stationary states through solvent exchange, the polyrotaxane monolith not only exhibits macroscopic shape-memory properties but is also capable of converting the chemical energy input into mechanical work by lifting objects against gravity.

Introduction

Mechanically interlocked molecules (MIMs),[1] including rotaxanes[2] and polyrotaxanes,[3] catenanes,[4] and molecular knots,[5] have been widely applied in the advancement of molecular shuttles,[6] switches,[7] muscles,[8] and pumps,[9] where light or chemical energy can be converted into molecular motions upon external stimuli. While great strides have been made in recent years, it remains challenging to incorporate MIMs into bulk materials such that their molecular motions can be effectively and cohesively transformed into the macroscopic scale.[10] The randomly oriented MIMs often counterbalance each other's mechanical work, thus affording no useful work macroscopically.[11] Controlling the spatial assembly[10a] of MIMs and synchronizing their mechanical motions[12] will amplify these molecular motions to a sizeable macroscopic event.[13] A recent development in this respect demonstrated,[14] by Harada et al., that the light-induced sliding motions of azobenzene/α-cyclodextrin (α-CD)-based [c2] daisy chains induce macroscopic actuation in both the dry and wet states of a hydrogel. Beside MIMs, Giuseppone et al. have also shown[15] that, by integrating light-driven unidirectional molecular rotors[16] into organogels, collective molecular motions can guide macroscopic contraction of the materials.

Developing functional materials by integrating MIMs into a defined three-dimensional (3-D) architecture[17] will allow rapid and effective amplification of molecular motions into macroscopic scale events.[18] This property, in turn, will allow the investigations of their macroscopic machinery behavior and the design, synthesis, and fabrication of complex smart devices which are currently beyond our grasp. Recently, with the help of additive manufacturing[19]—often referred to as 3-D printing—materials with integrated chemical[20] and biological functions[21] have been successfully fabricated into 3-D objects[22] and devices.[23] Integrating 3-D printability to MIMs will allow us to explore the possibility of amplifying solution-based molecular motions to the macroscopic level by taking advantage of the 3-D geometries with complex internal structures, for example, woodpile lattices in this research, which are not accessible using traditional manufacturing techniques. However, there is no precedent for a design rule to facilitate the 3-D printability of MIMs. Herein, we report the design and synthesis of printable polypseudorotaxane-based hydrogels (PRHs, FIG. 1) which are composed of α-CD rings and Pluronic F127 (PEO-PPO-PEO triblock copolymer; PEO=poly(ethylene oxide), PPO=poly(propylene oxide)) axles for direct-write 3-D printing.[24] By employing additional free α-CD rings to facilitate the hydrogen bonding network formed between the polypseudorotaxanes, we obtained PRHs possessing required shear-thinning and self-healing properties[25] for direct-writing. Photo-crosslinking the F127 axles after direct-writing affords polyrotaxane-based monoliths (PMs), with good 3-D structural integrity and mechanical stability by virtue of the formation of tubular arrays of α-CD rings and crystalline domains (FIG. 1), through the inter-ring hydrogen-bonding interactions[26] on the polymer backbone. Disrupting such interactions by a solvent exchange enables the α-CD rings to shuttle dynamically along the axles of the polyrotaxanes, and thus weakens the mechanical strength of the PM, and in turn, leads to a 3-D structural deformation. Re-establishing the inter-ring hydrogen-bonding interactions reconstitutes the 3-D structure of the PM, therefore allowing the amplification of the molecular shuttling motions of molecularly interlocked architectures into the macroscopic motion of the monolith through the conversion of chemical energy input into mechanical work.

We selected α-CD as the ring precursor because it forms polypseudorotaxanes[27] in the presence of polyethylene glycol (PEG) in aqueous solution as a result of inter-ring hydrogen-bonding interactions[26] as well as a favorable inclusion Gibbs free energy.[28] At a maximum (>90%) ring threading efficiency, as confirmed by molecular simulations [29] and experimental data,[26] the molar ratio of ethylene oxide (EO) repeating unit to α-CD (EO/α-CD) is approximately 2:1,[3c] where the α-CD rings orient in a head-to-head and tail-to-tail fashion.[30] In an α-CD/PEG4000 polyrotaxane,[31] the threading ratio is reported to be about 50% where EO/α-CD=4:1. In our design, to allow ring shuttling, Pluronic F127, containing PEO blocks of Mw=4400 Da at two termini, was selected as the axle precursor of the polypseudorotaxane to 1) achieve a moderate α-CD threading ratio and 2) form a hydrogel for direct writing, since Pluronic F127 is known to aggregate as micelles above its critical micelle concentration (cmc=2.8 mm).[32] After the addition of α-CD, and instead of employing bulky stopper precursors to prevent the rings from dethreading,[3c,33] the α-CDs will be mechanically interlocked by the polymerization of the methacrylate end groups of the Pluronic F127 axles (F127-MA$_2$; FIG. 1), thus forming a crosslinked polyrotaxane network.[34]

One challenge associated with developing polypseudorotaxane-based inks for direct writing is to tailor their rheological properties. That is, the printing inks ought to be able to flow through the nozzle during the direct-writing process and rapidly recover their mechanical strength afterward. In other words, the α-CD/Pluronic F127-based polypseudorotaxane hydrogels are required to possess shear-thinning and rapid self-healing properties [25] to allow successful 3-D printing. Although the preparation and rheological behaviors of some PRHs have been investigated,[35] the concentrations of Pluronic F127 in those PRHs are too high (10% w/v and above) for our design, because a densely crosslinked hydrogel formed by photo-crosslinking of a high concentration of F127-MA$_2$ will be too rigid and overpower any polyrotaxane molecular behaviors at a macroscopic scale. In addition, the self-healing capabilities of PRHs are largely unexplored. Therefore, it is important to reduce the F127 concentration for gelation while maintaining the viscoelastic properties of PRHs.

Figure 3A:
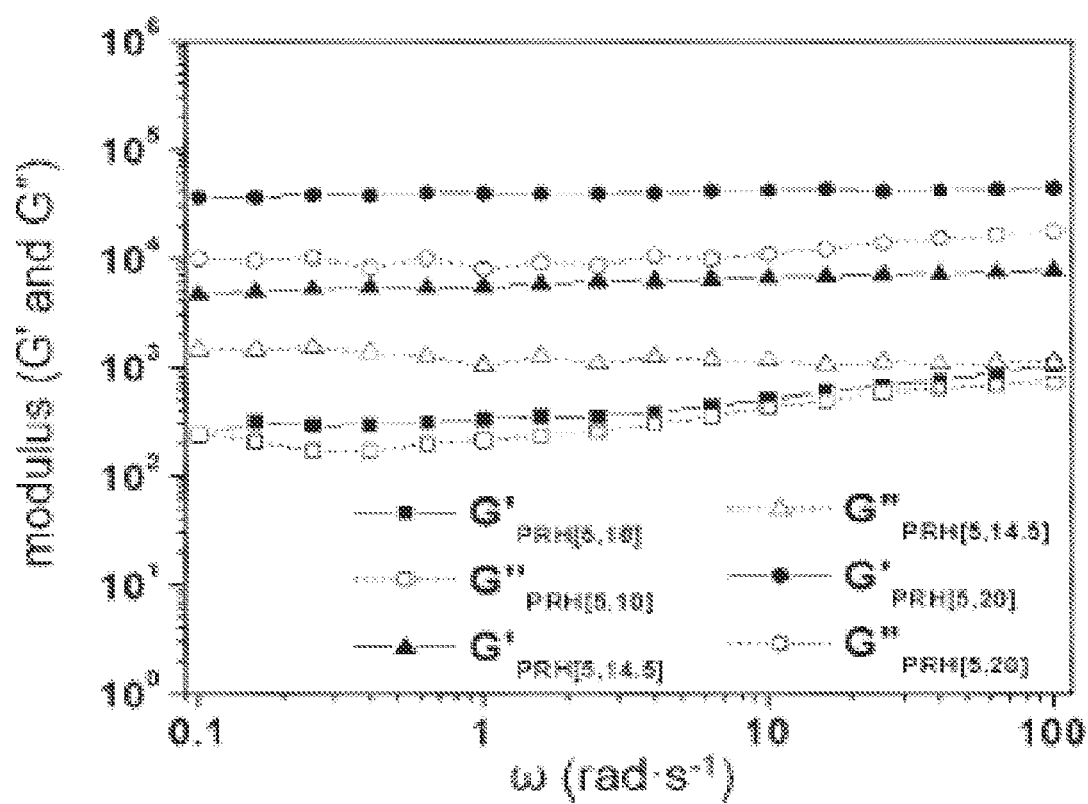
FIG. 3A. Variations of storage (G') and loss (G") moduli of PRH [5,10], PRH [5, 14.5] and PRH [5, 20] at different oscillation frequencies, respectively.

Methacrylated F127 (F127-MA$_2$) was synthesized from commercially available Pluronic F127 in 86% yield. 2,2-Dimethoxy-2-phenylacetophenone[36](DMPA) and N-vinylpyrrolidone (VP) were employed[37] as a photoinitiator and solubilizing agent, respectively (FIG. 1). A series of α-CD/F127-based polypseudorotaxanes were prepared (FIG. 2 and FIG. 10) and their rheological properties were investigated systematically (FIGS. 11-14). The storage (elastic, G') and loss (viscous, G") moduli of a PRH[10, 14.5] (the numbers within the brackets represent the concentrations of F127-MA$_2$ and α-CD in % w/v, respectively), prepared in an aqueous solution of α-CD, were measured (see FIG. 11) to be 3919 Pa and 594 Pa (at 0.1% strain), respectively. To our surprise, reducing the concentration of the axle precursor F127-MA$_2$ did not result in decreased G' and G" of the obtained PRHs. In contrast, PRH[7.5, 14.5] and PRH[5, 14.5] exhibit plateau values of G' ~5400 and ~7600 Pa, respectively. To reveal the gelation mechanism, PRH[5, 10-20]s with various amounts of α-CDs were prepared. As shown in FIG. 3A, the storage moduli G' of the PRHs increases 12 times when the α-CD concentration is increased from 10 to 20% w/v, thus indicating that the formation of polypseudorotaxanes greatly improves the viscoelastic properties of the PRHs. In addition, the formation of microcrystalline domains[38] between polypseudorotaxanes (FIG. 1) act as supramolecular crosslinkers, which further strengthen the obtained hydrogel.

Figure 3B:
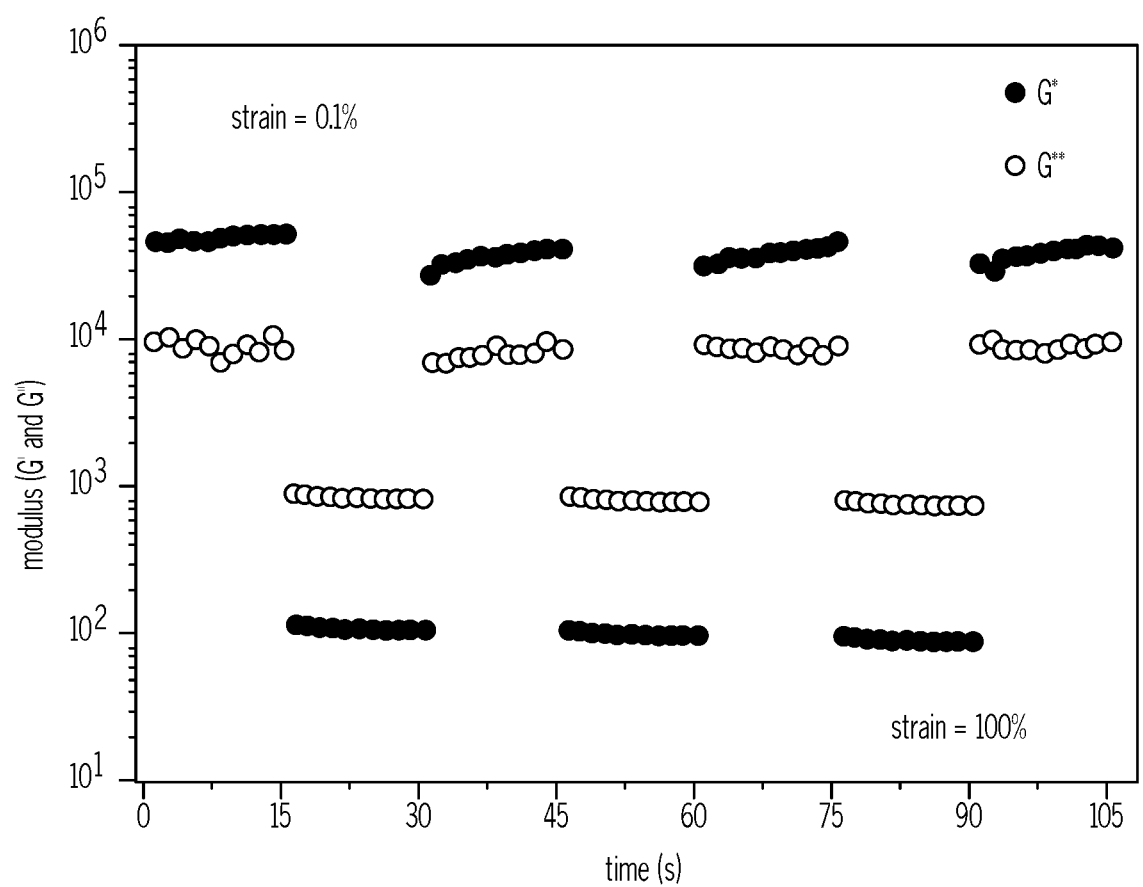
FIG. 3B. Alternative step-strain relaxation test of PRH [5,20] at room temperature.
Figure 4A:
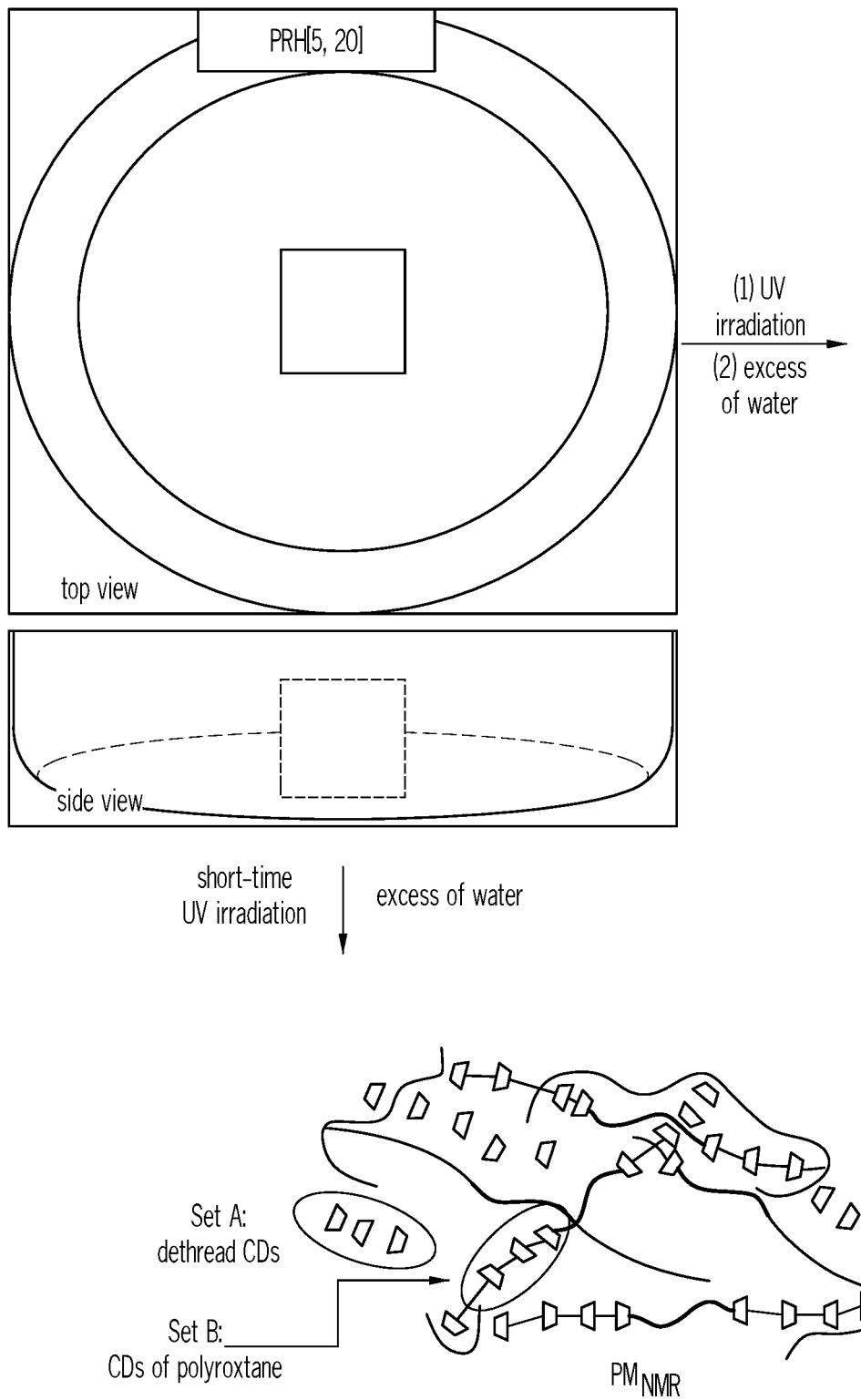
FIG. 4A. Top and side views of a wood-pile lattice cube fabricated using PRH[5,20] after direct writing, photopolymerization (CM) and soaking in DMSO and water.
Figure 4B:
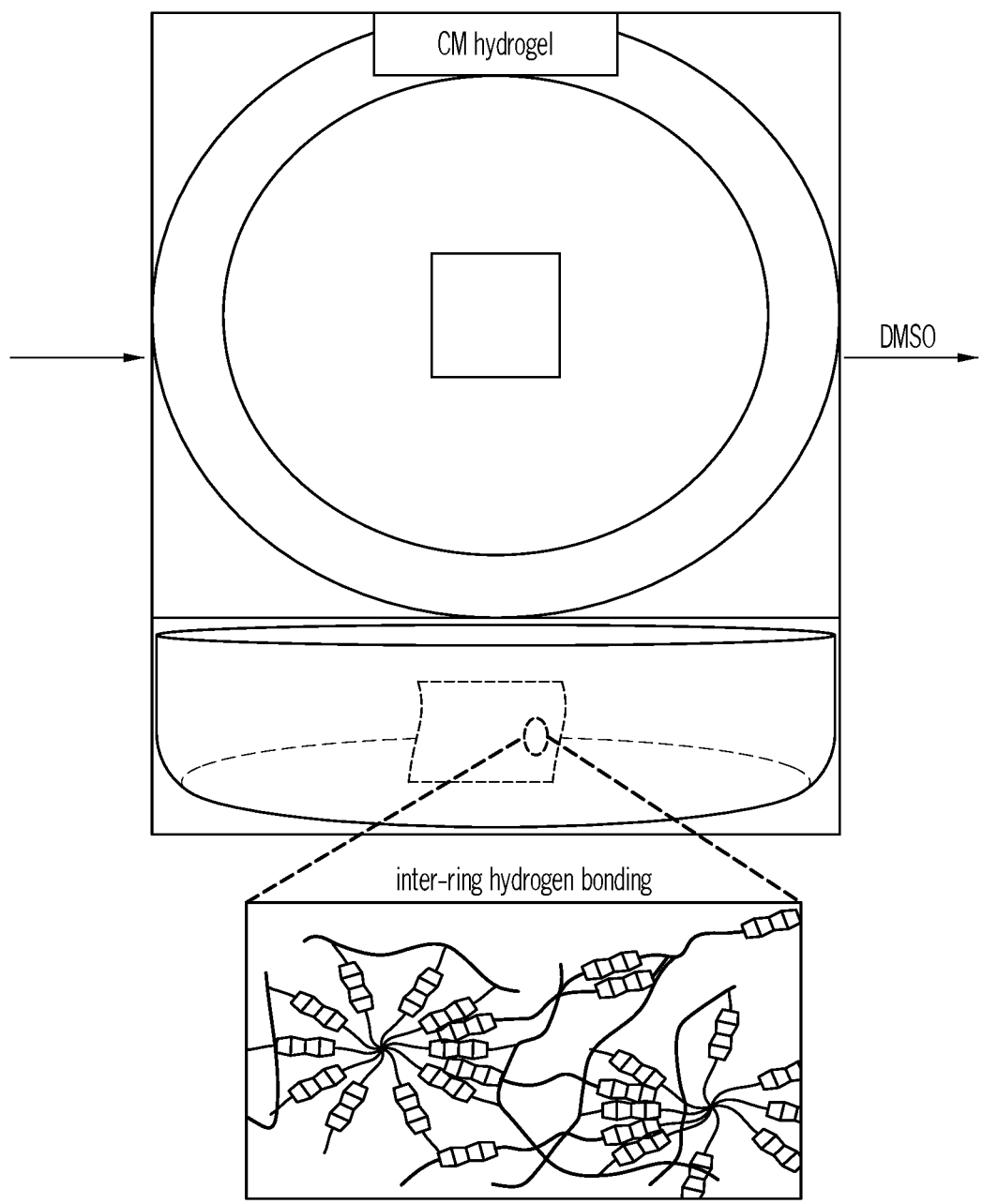
FIG. 4B. Top and side views of a wood-pile lattice cube fabricated using PRH[5,20] after direct writing, photopolymerization (CM) and soaking in DMSO and water.
Figure 4C:
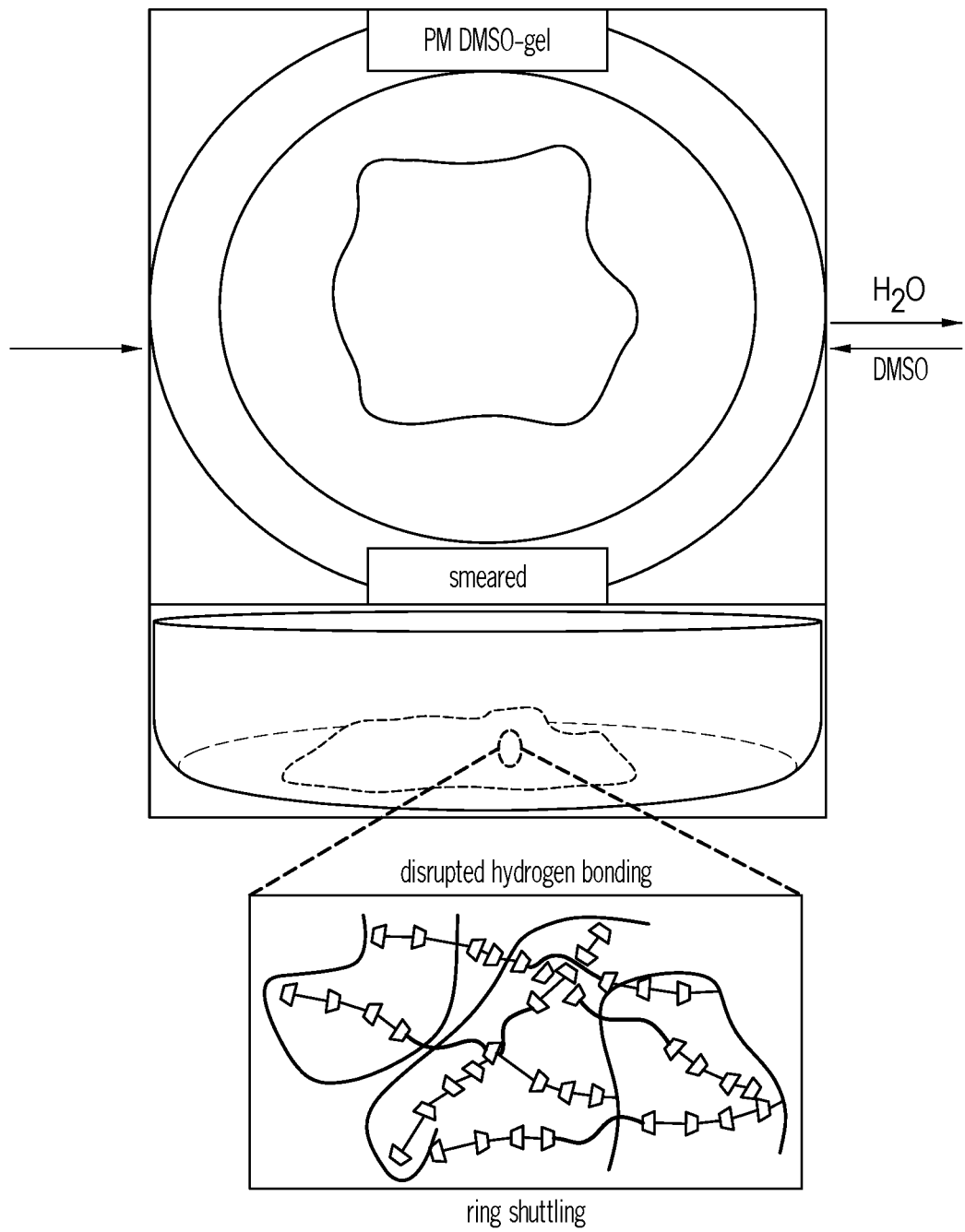
FIG. 4C. Top and side views of a wood-pile lattice cube fabricated using PRH[5,20] after direct writing, photopolymerization (CM) and soaking in DMSO and water.
Figure 4D:
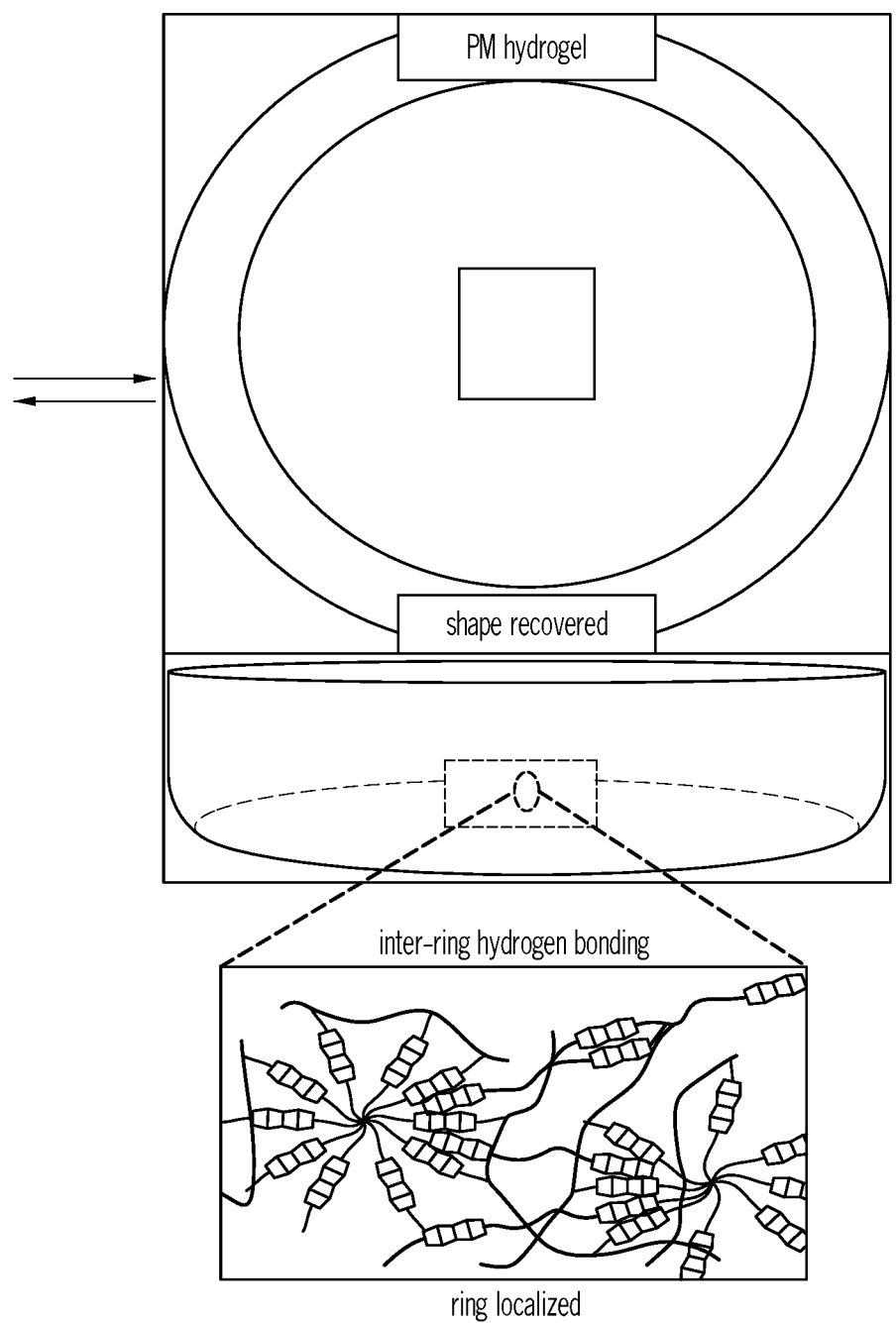
FIG. 4D. Top and side views of a wood-pile lattice cube fabricated using PRH[5,20] after direct writing, photopolymerization (CM) and soaking in DMSO and water.

Although the prepared PRHs exhibit shear-thinning properties (see FIG. 13), most of them were not, in practice, suitable for direct writing. As-printed 3-D lattice cubes quickly lost their 3-D features by smearing into a puddle, thus suggesting that these PRHs cannot recover their elastic properties upon shear force. These observations are consistent with the results of the alternate step-strain relaxation experiments (see FIG. 14). For example, after applying a large stress (100% strain) in each cycle, the storage modulus G' of PRH[5, 10] and PRH[5, 14.5] at 0.1% strain exhibited significant loss compared to the previous cycle (see FIG. 14). (N.B. Although these PRHs could not recover their elastic moduli rapidly, they could recover their viscoelastic properties after 4-12 hours.) Interestingly, G' of PRH[5, 20] (FIG. 3B) recovered to nearly 80% of its original value within 15 seconds after the first step-strain relaxation cycle and remained stable in the following cycles. These results suggest that the kinetics of the PRHs self-healing process is critical for successful direct writing. Based on the rheological studies, we hypothesized that the rapid self-healing of PRH[5, 20] may be attributed to 1) a high α-CD threading ratio in the formed polypseudorotaxanes and 2) an accelerated microcrystalline domain reformation which is facilitated by unthreaded α-CDs, both of which promote the rapid re-establishment of hydrogen-bonding networks.

Figure 5:
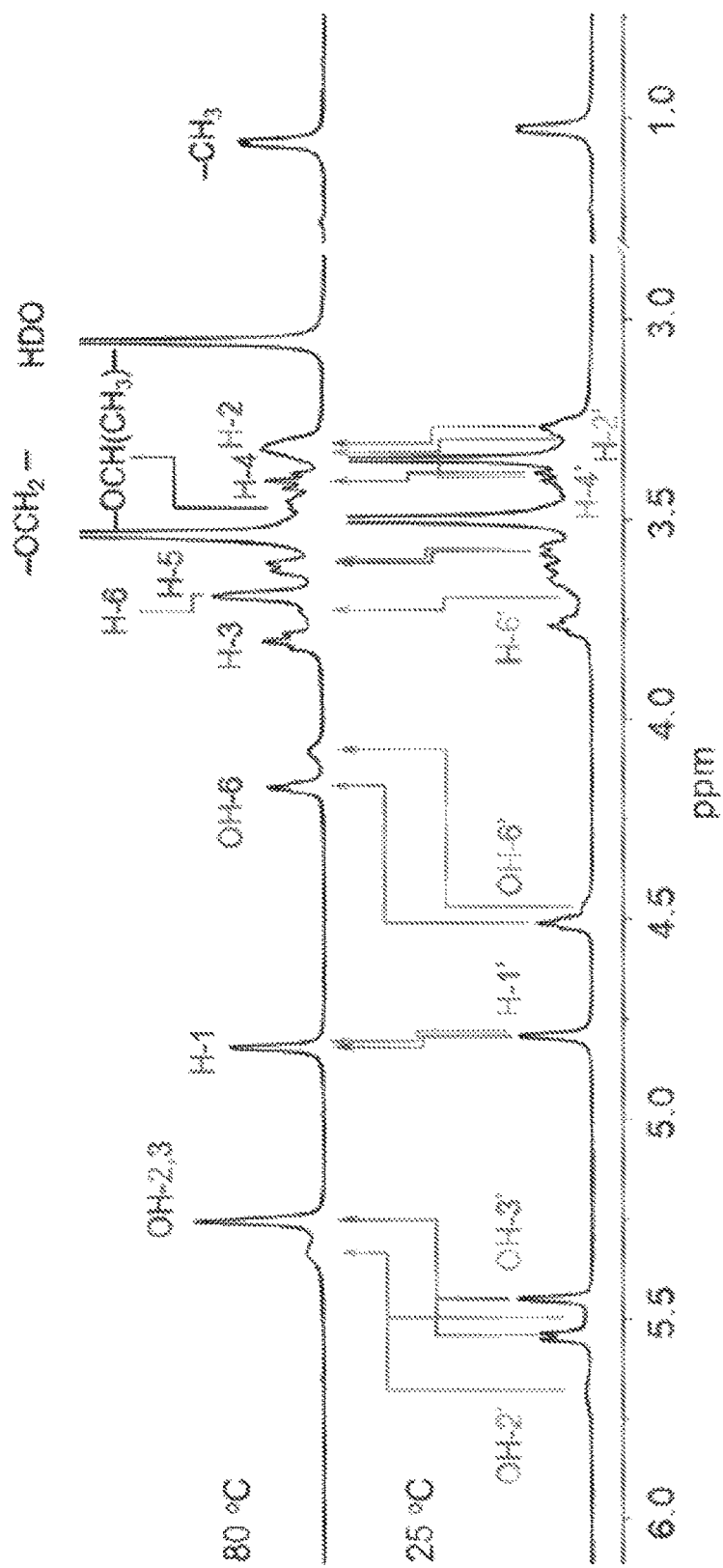
FIG. 5. $^1$H NMR spectra of a $PM_{NMR}$ in [$D^6$]DMSO at 25° C. and 80° C., respectively.
Figure 7:
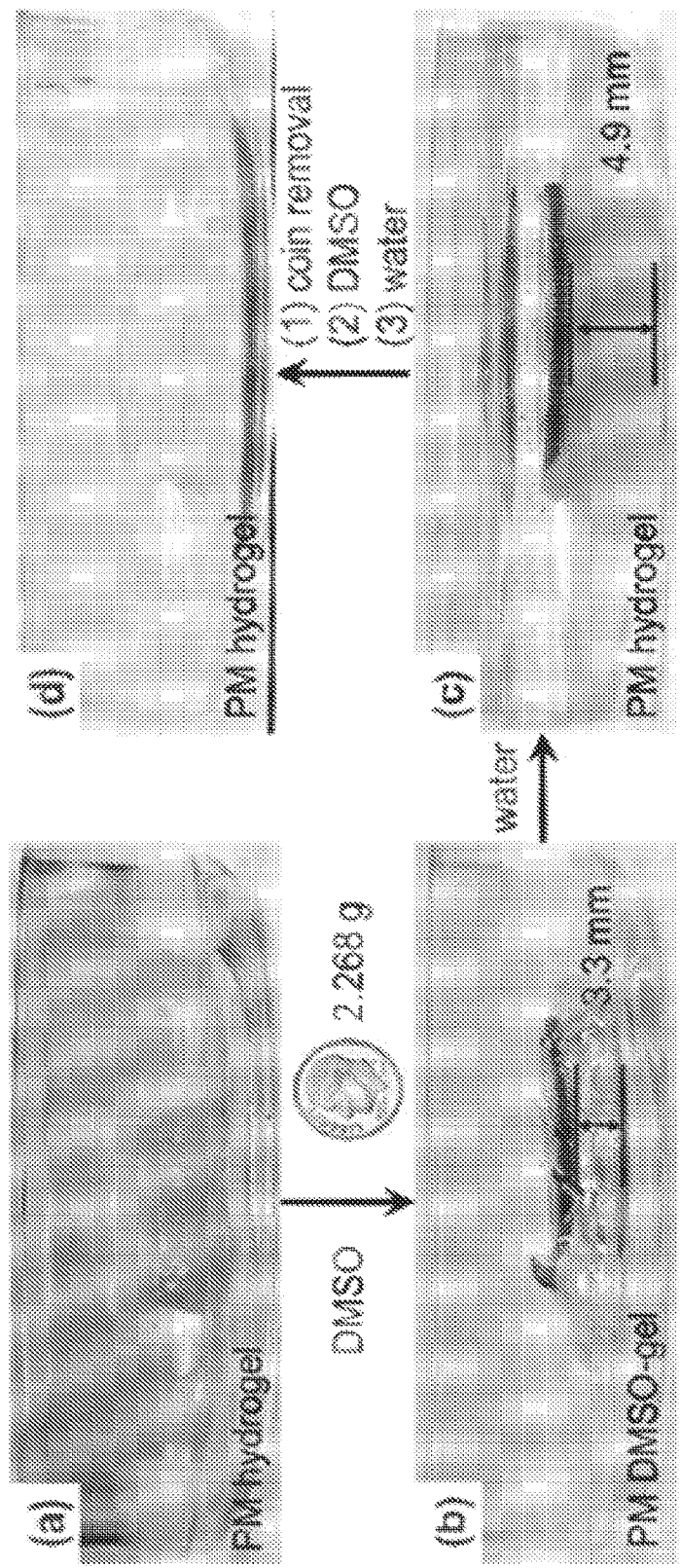
FIG. 7. A metal coin was lifted by a PM after the solvent exchange. The top left shows a side view of a PM hydrogel; bottom left shows a PM DMSO-gel with a US dime; bottom right shows a PM hydrogel with a US dime, and top right shows a recovered PM hydrogel after removal of the coin.
Figure 8:
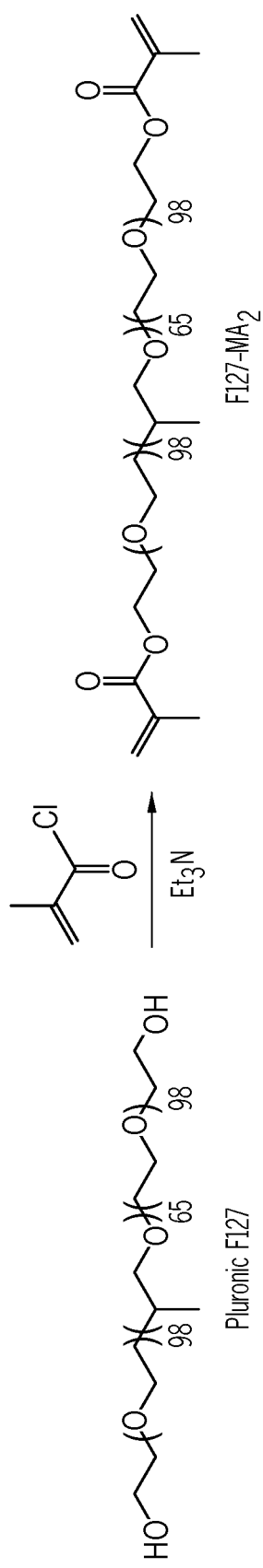
FIG. 8. Synthesis of telechelic polymer F127-MA$_2$.
Figure 9:
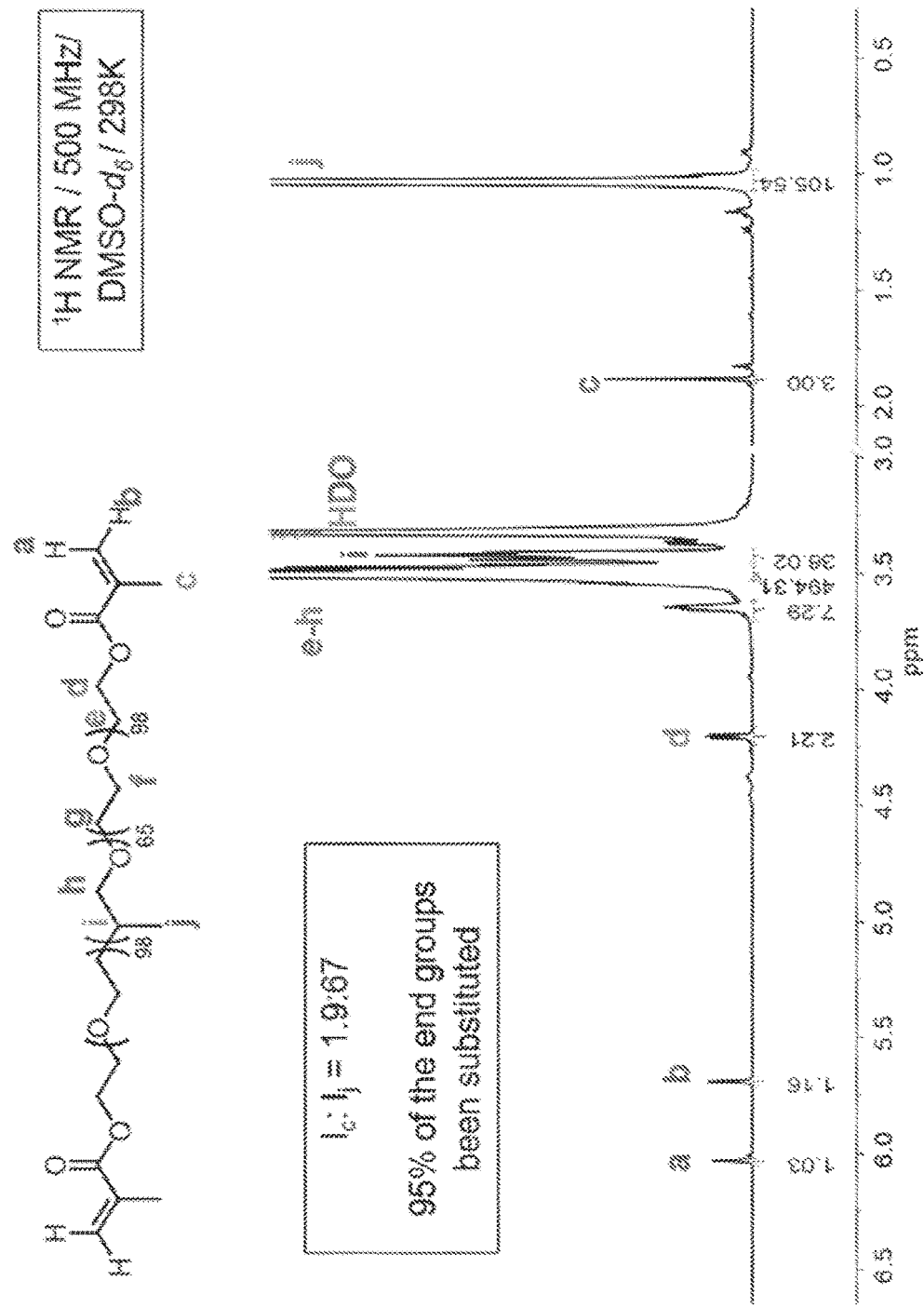
FIG. 9. $^1$H NMR spectrum (500 Hz) of a F127-MA$_2$ in [D$^6$]DMSO at 298K.
Figure 11:
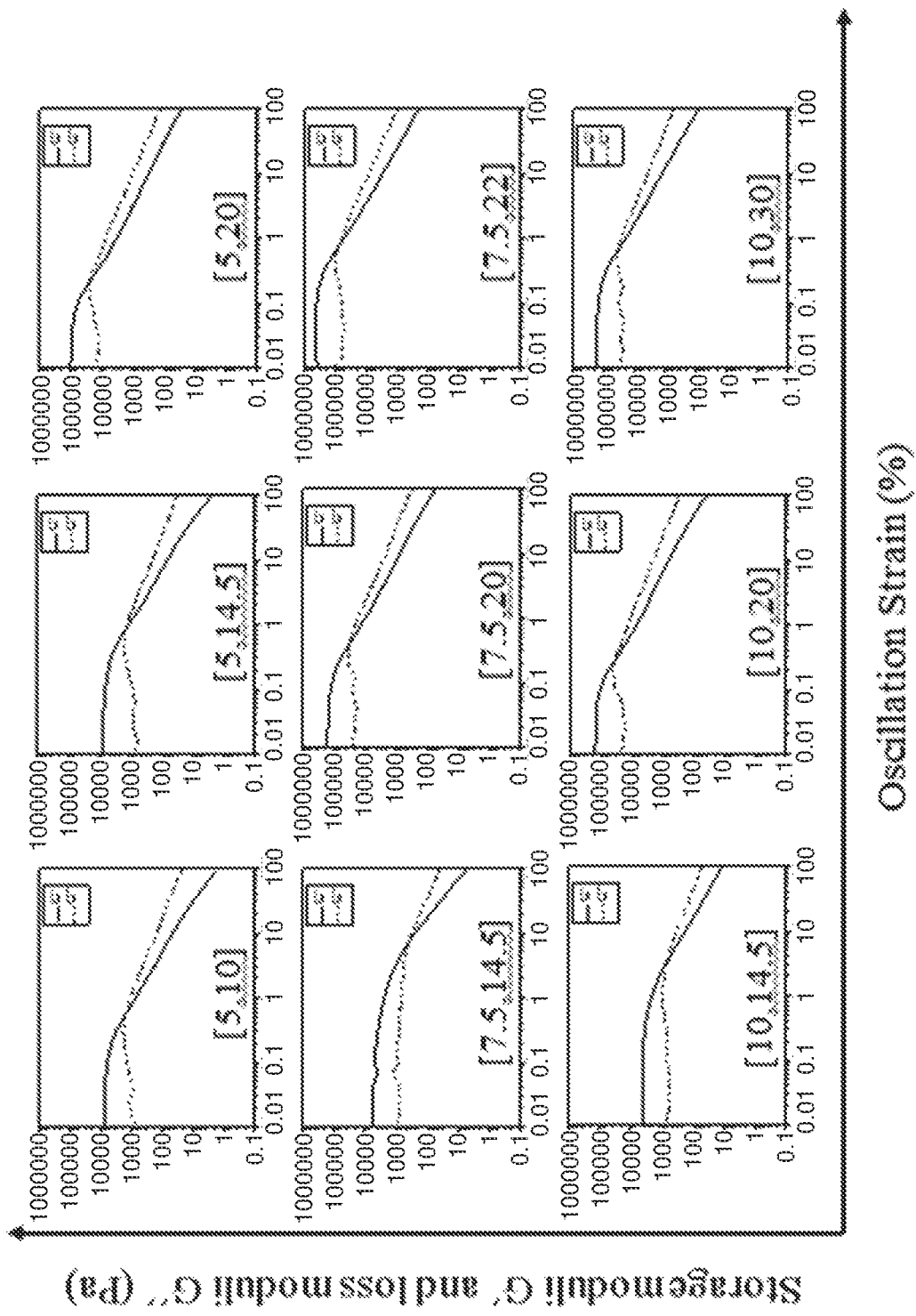
FIG. 11. Oscillation strain sweep profiles of PRHs listed in FIG. 10.
Figure 16:
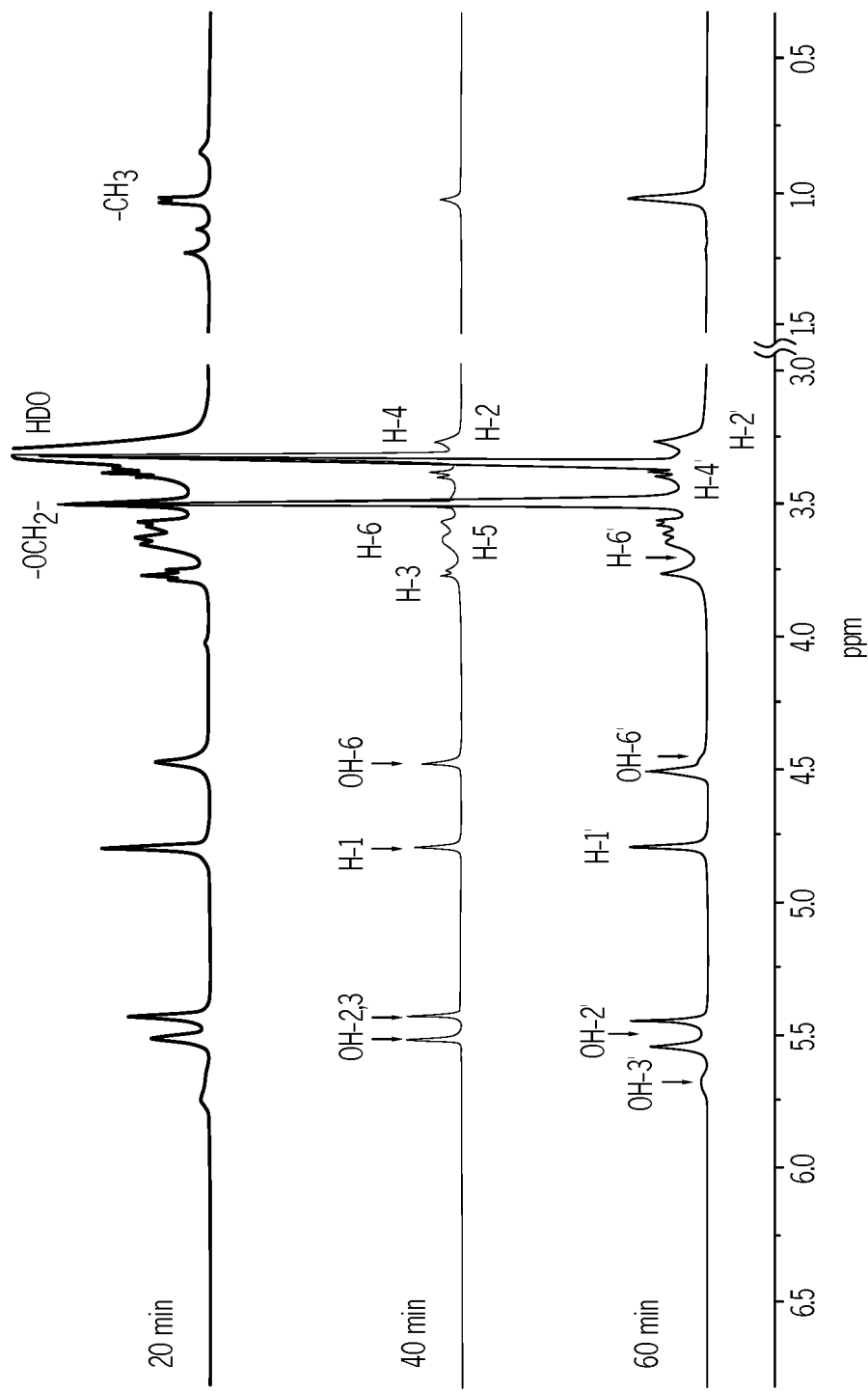
FIG. 16. $^1$H NMR spectra of PM$_{NMRS}$ recorded in [D$^6$] DMSO at 298K with different UV exposure time top, 20 mins, middle, 40 mins and bottom, 60 minutes.
Figure 17:
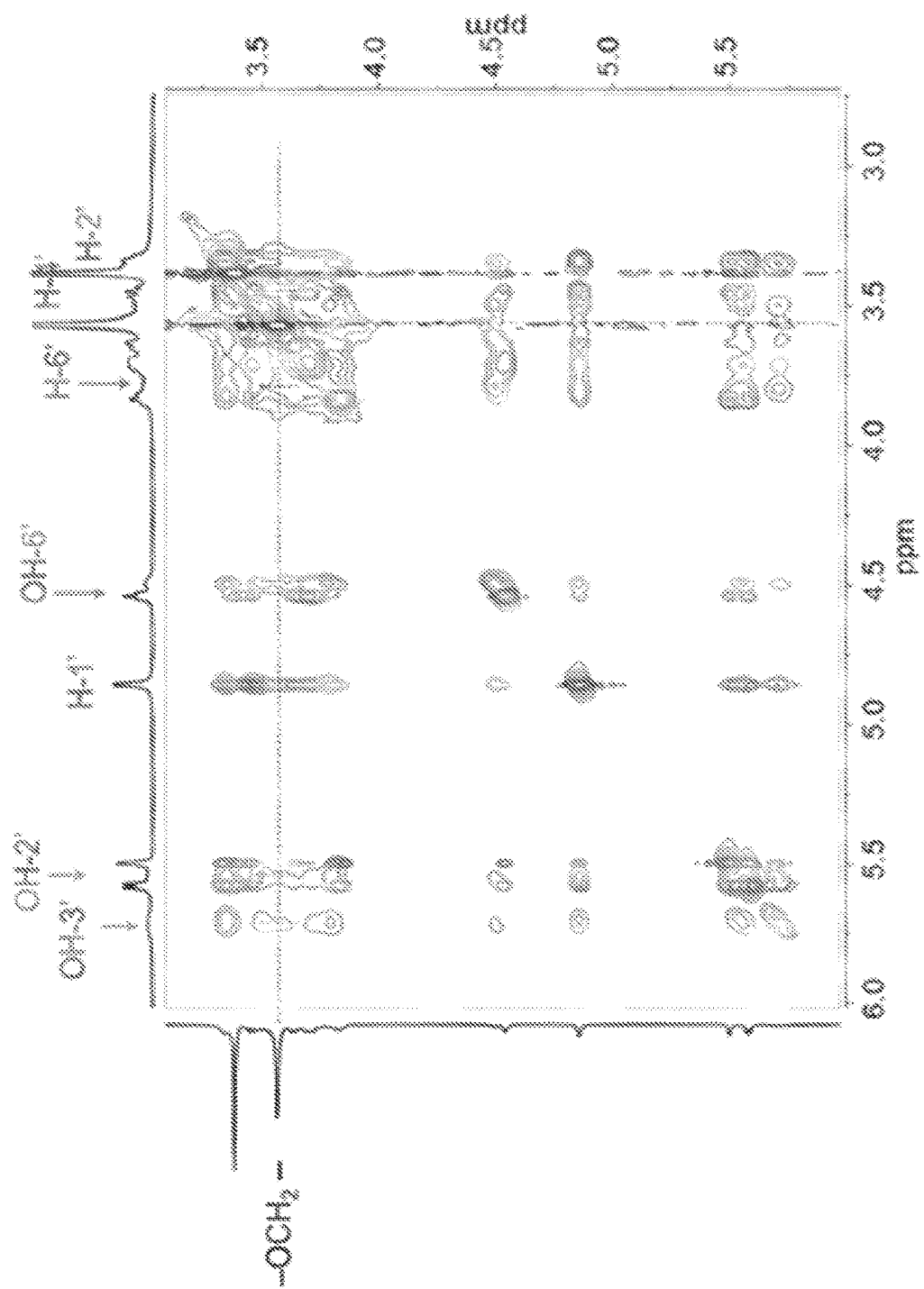
FIG. 17. $^1$H-$^1$H NOESY spectrum (mixing time+300 ms) of PM$_{NMR}$ in DMSO-d$_6$ at 298K.
Figure 18:
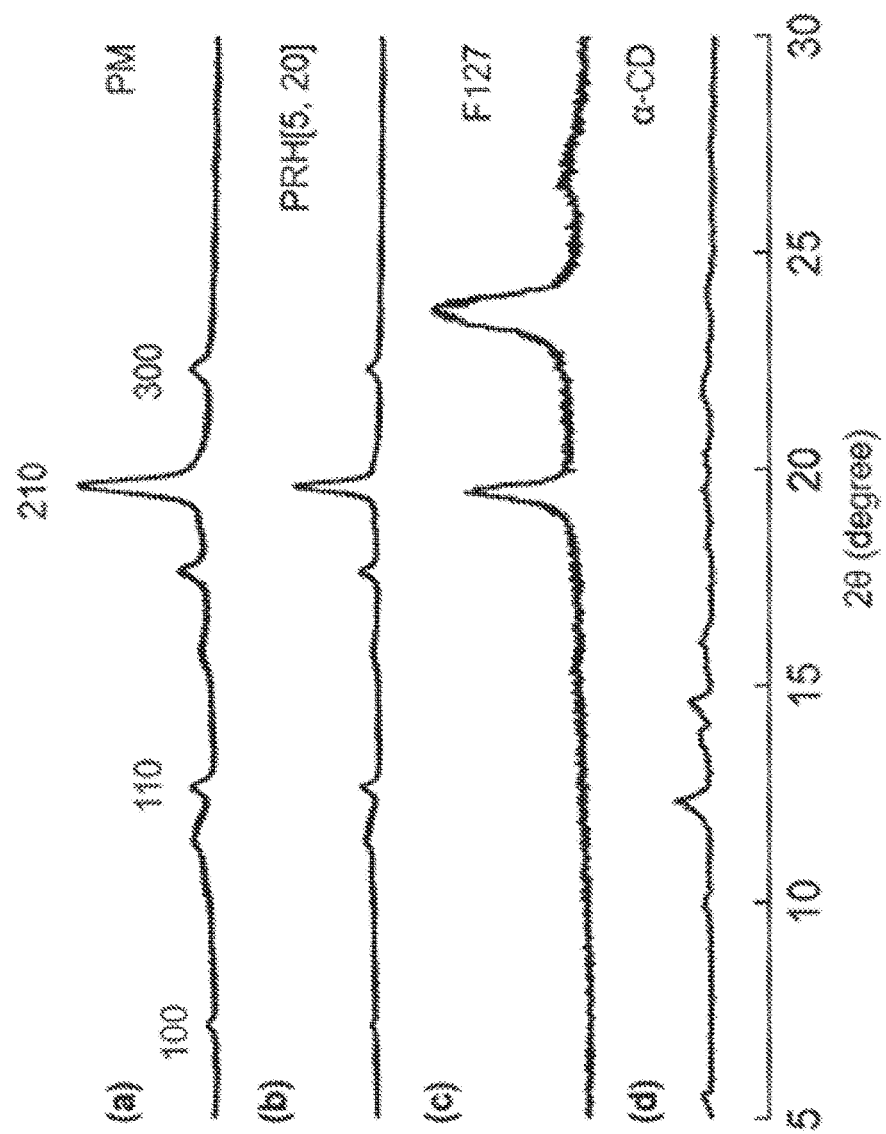
FIG. 18. PXRD diffraction patterns of the (top) PM, second from top, PRH[5,20], second from bottom, F127 and α-CD.
Figure 19:
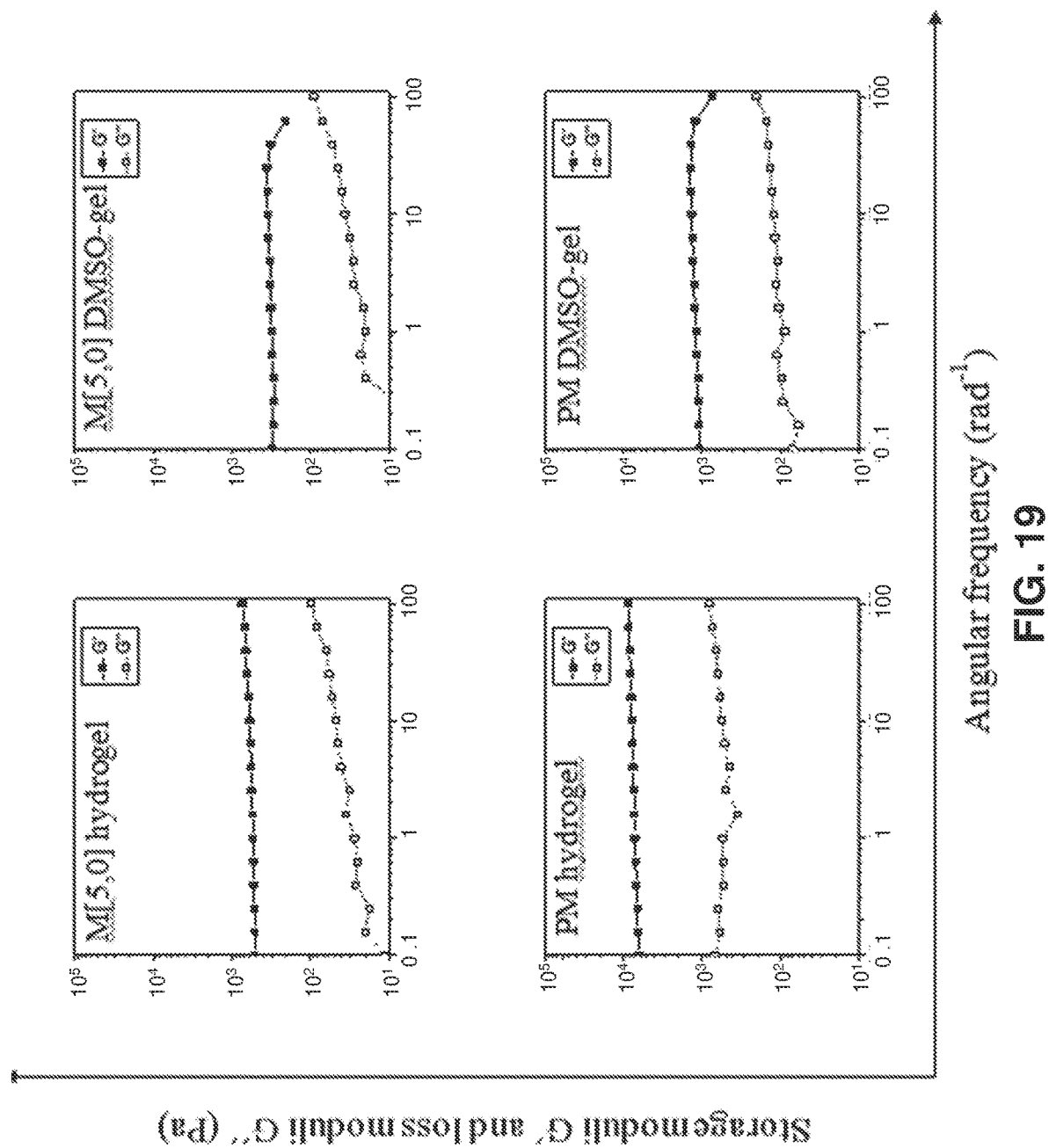
FIG. 19. Angular frequency sweep profiles of PM and M[5,0] in their hydrogel and DMSO-gel forms, respectively.
Figure 20:
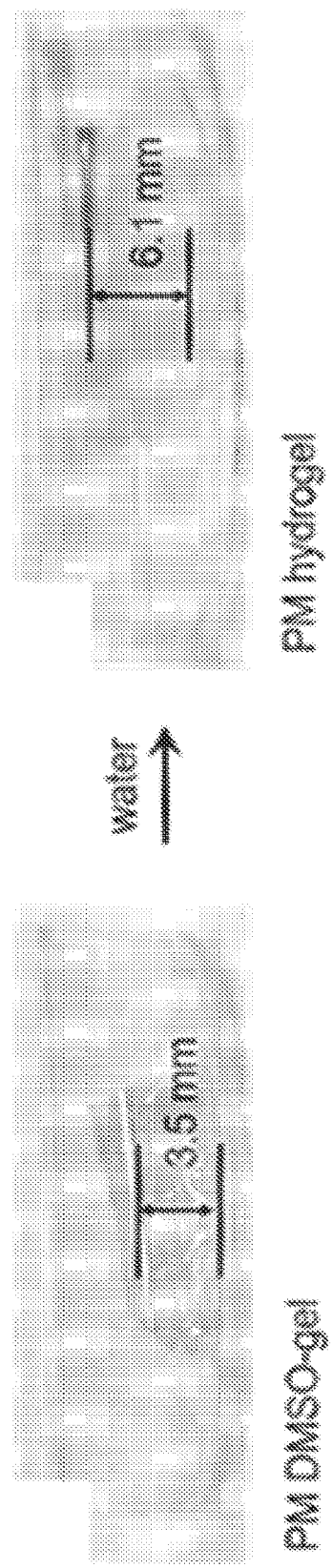
FIG. 20. An aluminum plate was lifted by a PM after the solvent exchange. Side view of (left) PM DMSO-gel with an aluminum plate and (right) PM hydrogel with the aluminum plate after shape recovery.

Cubic woodpile lattices with multiple orthogonal layers of parallel cylindrical filaments were fabricated layer-by-layer (FIG. 7) using PRH[5, 20]. The fabricated cubic lattices exhibit good structural integrity and accuracy in all x, y, and z dimensions (9×9×6 mm). After direct writing, the lattice cubes were irradiated with UV light followed by washing to afford crosslinked monoliths (CMs, FIG. 7, bottom left). In both PRH[5, 20] and CM, α-CD rings are interconnected by hydrogen-bonding networks to form tubular arrays, which further aggregate to form hexagonal crystalline domains[40] as confirmed by powder X-ray diffraction (PXRD) experiments (see FIG. 18). These hierarchical tubular arrays and microcrystalline domains act as rigid supramolecular struts and noncovalent crosslinkers, respectively, which stabilize the 3-D superstructures of the CM. Disrupting the inter-ring hydrogen-bonding interactions using a solvent such as DMSO will dismantle the crystalline domains as well as the tubular arrays, where the α-CD rings will shuttle along the axles. After soaking the opaque CM lattice cube in DMSO for 24 hours, the 3-D structure of the polyrotaxane monolith (PM) was deformed into a puddle of transparent DMSO-gel (FIG. 7, bottom right). The significant structural deformation is a result of 1) the disassembly of tubular α-CD polyrotaxane arrays and polyrotaxane crystalline domains, thus decreasing the rigidity of the polyrotaxane network, 2) a subsequent swelling enabled by the free-shuttling α-CD rings, since disruption of inter-ring interactions allows DMSO to extensively solvate the rings and axles of the monolith (see FIG. 7, right top; FIG. 21), and 3) designed 3-D structure with macroscopic void spaces. The disrupted α-CD ring interactions could be re-established rapidly. As shown in FIG. 7, top right), within two hours of being immersed in water, PM recovered its original 3-D shape. This process occurs in two stages: 1) a rapid shape recovery in the vertical direction, thus indicating a rapid reformation of tubular arrays of α-CD rings upon solvent exchange and 2) a gradual transformation from a transparent gel back into an opaque hydrogel, as a result of the reformation of the microcrystalline domains. Therefore, by restricting the ring motions on the axle of the polyrotaxane, we could re-establish the mechanical properties of the 3-D-printed monolith. This shape changing and recovery behavior of PM is highly reversible and can be easily repeated five times. We also noticed that the size of the PM after shape recovery is about 30% larger (11×11×7 mm) than the lattice cube produced using PRH[5, 20]. To confirm the formation of PM, reveal the α-CD threading ratio, and investigate the dynamic motions in the polyrotaxane, we synthesized PMs with low degrees of crosslinking (PM$_{NMR}$; see FIG. 16) for $^1$HNMR analysis. Two sets (Set A and Set B, FIG. 5) of α-CD proton resonances were observed in the $^1$H NMR spectrum at 25° C. These two sets of CD proton resonances did not interchange when the solution was heated to 80° C. In the NOESY spectrum (see FIG. 17) recorded at 298K, correlation peaks were observed between the ethylene protons of the EO and Set B (FIG. 5) α-CD protons but not Set A, thus suggesting that set A α-CDs are "free" rings whereas set B α-CDs are the rings of the polyrotaxane. The hydroxy proton resonances of set B became narrower at 80° C., thus suggesting that the shuttling motion of α-CD rings accelerates upon heating. These results reveal that the "free" CD rings observed in the NMR experiments are ones that had dethreaded from polypseudorotaxanes and CM is composed of a mixture of polyrotaxanes and polypseudorotaxanes. The ratio of the CD (set A+B; FIG. 5) proton resonances and those of the PEO block of F127-MA$_2$ suggest approximately 33:7 CD rings are threaded on each F127 axle with a threading ratio of about 33% (EO/α-CD=6:1). The threading ratio is lower than the feeding ratio (53%) of PRH, thus suggesting about 62% of the α-CD rings are threaded on the axle to form the polypseudorotaxane, leaving about 38% of the free α-CD rings in the PRH[5, 20], and confirming our hypothesis in the rheological studies. After being soaked in DMSO, the unstopped CD rings in CM are removed, thus affording a PM composed of polyrotaxanes and bare F127 side chains. Elemental analysis of PM reveals a CD:F127 ratio of 19:5:1, which corresponds to a polyrotaxane/F127 side-chain ratio of 1.4:1. The loss of rings results in a less dense hydrogen bonding network within the PM, and explains our earlier observation that PM is larger than PRH[5, 20] and CM.

Figure 6:
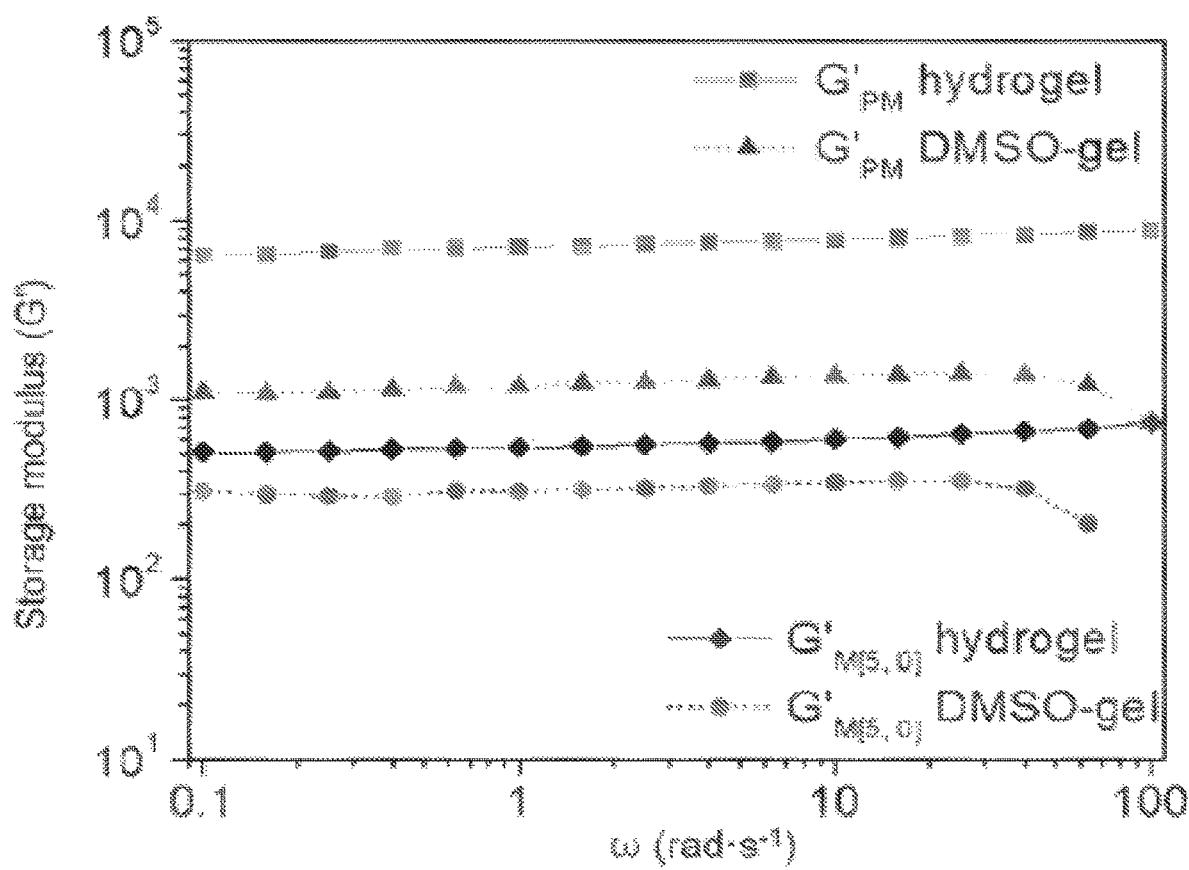
FIG. 6. Storage moduli of PM hydrogel (square) and DMSO gel (triangle), M[5,0] hydrogel (diamond) and DMSO gel (dot), respectively.

To reveal the mechanism of shape changing at a molecular level, we synthesized a hydrogel monolith M[5, 0] by photoirradiating a F127-MA$_2$ micellar solution (5% w/v) in the absence of α-CDs (see the Supporting Information) in a mold. The G' of M[5, 0] decreases moderately (FIG. 6) after solvent exchange from water to DMSO, thus suggesting the PPO block of F127 backbone has limited contribution to the overall elasticity of gel M[5, 0]. The G' changing ratio of PM in the forms of hydrogel and DMSO-gel (ΔG'/G' hydrogel=83%, where ΔG'=G'$_{hydrogel}$-G'$_{DMSO-gel}$) is significantly larger than that of M[5, 0] (ΔG'/G'$_{hydrogel}$=43%). These results reveal that the formation of tubular α-CD ring arrays and microcrystalline domains in PM greatly enhances its mechanical property in the hydrogel form. In addition, DMSO could effectively disrupt the hydrogen-bonding interactions between α-CD rings, thus resulting in random ring-shuttling motions in PM, thereby reducing its mechanical property. This dramatic mechanical property switching of PM is enabled by the installation of mechanical bonds.

The microscopic conversion from ring-shuttling motion into ring-localization not only enables the macroscopic shape recovery but also facilitates the transformation of chemical energy, in the form of solvent exchange, into mechanical work. As shown in FIG. 7, upon adding water to the smeared PM DMSO-gel, a 2.268 g US dime (or an aluminum plate, not shown) has been lifted 1.6 mm in the vertical direction, thus producing 30.5 mJ of work (FIG. 7). The PM hydrogel kept its shape (4.9 mm height) after removal of the coin, thus suggesting that a metastable polyrotaxane network was formed in the presence of mechanical force. This metastable PM-hydrogel (FIG. 7) recovered its original state (FIG. 7) after another solvent exchange cycle, by breaking and reforming the hydrogen-bonding network between α-CD rings, thus rendering PMs as reversible shape-memory[41] materials.

In summary, we have successfully integrated mechanically interlocked architectures into 3-D printing materials and developed polypseudorotaxane-based hydrogels possessing shear-thinning and self-healing properties. After post-printing polymerization, the obtained polyrotaxane monolith reversibly deforms and reforms its complex 3-D structure by solvent exchange, which is enabled by switching the threaded α-CD rings between random shuttling and stationary states at the molecular level. When the polyrotaxane monolith is converted from a DMSO-gel into a hydrogel form, the 3-D printed monolith is capable of lifting objects vertically, therefore converting the external energy input into mechanical work. Our system demonstrates how molecular level motion can be used in the control of macroscopic motion in a complex 3-D object. This advancement will enable scientists to further develop mechanically interlocked molecule-based smart materials and devices.

Experimental Section
Materials and Methods.

All reagents were purchased from commercial suppliers (Acros and Alfa) and used as received without further purifications. α-Cyclodextrin was generously gifted by Wacker Chemical Corp. PLURONIC F127 was purchased from Sigma and was dried under reduced pressure at 60° C. for 24 H. Nuclear magnetic resonance (NMR) spectra were measured on BURKER ASCEND 600 or OXFORD NMR 500 spectrometers.

Synthetic Procedures
Scheme S1. Synthesis of Telechelic Polymer F127-MA$_2$

F127-MA$_2$: F127-MA$_2$ was synthesized according to a previously reported method.[D. Ma, X.-Y. Zhou, Y.-F. Yang, Y. You, Z.-H. Liu, J.-T. Lin, T. Liu, W. Xue, Science of Advanced Materials 2013, 5, 1307-1315.] In a 100 mL round bottom flask, PLURONIC F127 (12.6 g, 1 mmol) was dissolved in anhydrous CH$_2$Cl$_2$ (50 mL) and the reaction was cooled to 0° C. in an ice bath. Methacryloyl chloride (0.69 mL, 6 mmol) and triethylamine (0.99 mL, 6 mmol) were added to the F127 solution dropwise over 30 min and the reaction mixture was stirred for another 24 h. The crude product was extracted by CH$_2$Cl$_2$ (450 mL) followed by washing with H$_2$O (50 mL), saturated NaHCO$_3$ aqueous solution (50 mL), and H$_2$O (50 mL), respectively. The organic phase was collected and the solvent was removed under the reduced pressure. The crude product was re-dissolved in CH$_2$Cl$_2$ (50 mL) and precipitated using an excess of diethyl ether. The final product was collected by filtration and dried at 40° C. under vacuum for 24 h, affording F127-MA$_2$ as a white powder in 86% yield. $^1$H NMR (500 MHz, DMSO-d6, 298K): δ=6.03 (t, J=1.3 Hz, 1H), 5.69 (p, J=1.7 Hz, 1H), 4.24-4.16 (m, 2H), 3.71-3.62 (m, 7H), 3.51 (bs, 494H), 3.42 (ddd, J=7.9, 5.7, 2.0 Hz, 36H), 1.88 (t, J=1.3 Hz, 3H), 1.03 (dd, J=6.2, 1.7 Hz, 106H).

S3. General Methods for the Preparation of Polypseudorotaxane Hydrogels (PRHs)

Preparation of PRHs. In this study, PRHs containing different molar ratios of F127-MA$_2$ to α-CD were prepared as listed in FIG. 10. Typically, α-CD was dissolved in water at 50° C. before F127-MA$_2$ was added. After F127-MA$_2$ was dissolved completely, the reaction was stirred for an additional 4 h at 50° C. to allow the formation of polypseudorotaxane. The reaction was then cooled to room temperature and an opaque hydrogel was obtained. The hydrogel was consolidated for 12 h before the rheological studies and 3-D printing experiments.

Preparation of PRH[5, 20] with photo-initiator. Firstly, an aqueous 20% w/v α-CD solution was prepared by dissolving α-CD (2 g, 2.0 mmol) in water (10 mL) at 50° C. Telechelic polymer F127-MA$_2$ (0.5 g, 0.04 mmol) was added to the α-CD solution and the reaction was stirred until F127-MA$_2$ was dissolved completely. The obtained solution was stirred for an additional 4 h at 50° C. before a 2,2-dimethoxy-2-phenylacetophenone (DMPA) (24 mg, 0.094 mmol) in N-vinylpyrrolidone (VP) (40 µL) solution was added. The reaction was kept in the dark, cooled down to room temperature and consolidated for 12 h before direct-writing.

S4. Rheological Studies of the PRHs

Methods: Rheological measurements were performed on a stress-controlled rheometer (TA instruments, DHR-2) with a 20-mm diameter parallel plate geometry and a measuring gap of 1 mm at room temperature. All PRH samples were consolidated for 12 h at room temperature before the analysis. Oscillation strain sweep test: Strain sweep tests were performed to investigate the linear viscoelastic regions of the obtained PRHs at 25° C. The oscillation strain was increased from 0.01% to 100%. The angular frequency was set at 1 rad/s (frequency=0.16 Hz).

Angular frequency sweep test: Angular frequency sweep tests were performed to investigate the elastic (storage) and viscous (loss) moduli at 25° C. The angular frequency was increased from 0.1 rad/s to 100 rad/s (frequency increased from 0.016 Hz to 15.92 Hz). Based on the results of oscillation strain sweep experiments, the oscillation strain was set at 0.1%.

Steady rate sweep test: Steady rate sweep tests were carried out to investigate the shear-thinning behaviors of the PRHs at 25° C. The shear rate was increased from 1 s−1 to 100 s−1.

Dynamic step-strain amplitude test: Dynamic step-strain amplitude tests were performed to investigate the self-healing properties of the PRHs. The oscillation strain applied were 1% and 100% in each cycle at 1 rad/s angular frequency. The duration of strain at each step was 15 s.

Discussion: In order to map the viscoelastic properties of PRHs and their 3-D printability, a series of rheological experiments were carried out as mentioned above.

In the oscillation strain sweep experiments (FIG. 11), the storage moduli G' of PRHs at low oscillation strain were recorded larger than their loss moduli G". The elastic moduli of PRHs are independent of the concentration of F127-MA$_2$, suggesting the formation of the polypseudorotaxane is the predominate factor in the hydrogel formation. PRH[10, 14.5] possesses a yield strain (where G'=G") of 3%, at which point the noncovalent interactions were extensively disrupted. The yield strain decreased when the α-CD concentration was increased. Similar observations were recorded in PRHs[7.5, 14.5-22] and PRHs[5, 10-20]. These results suggest that increasing the α-CD concentration could effectively prompt the formation of polypseudorotaxanes and the subsequent polypseudorotaxanes crystalline domains, which deforms at lower strain according to the theoretical model. [W. Y. Shih, W. H. Shih, I. A. Aksay, Journal of the American Ceramic Society 1999, 82, 616-624.]

Figure 12:
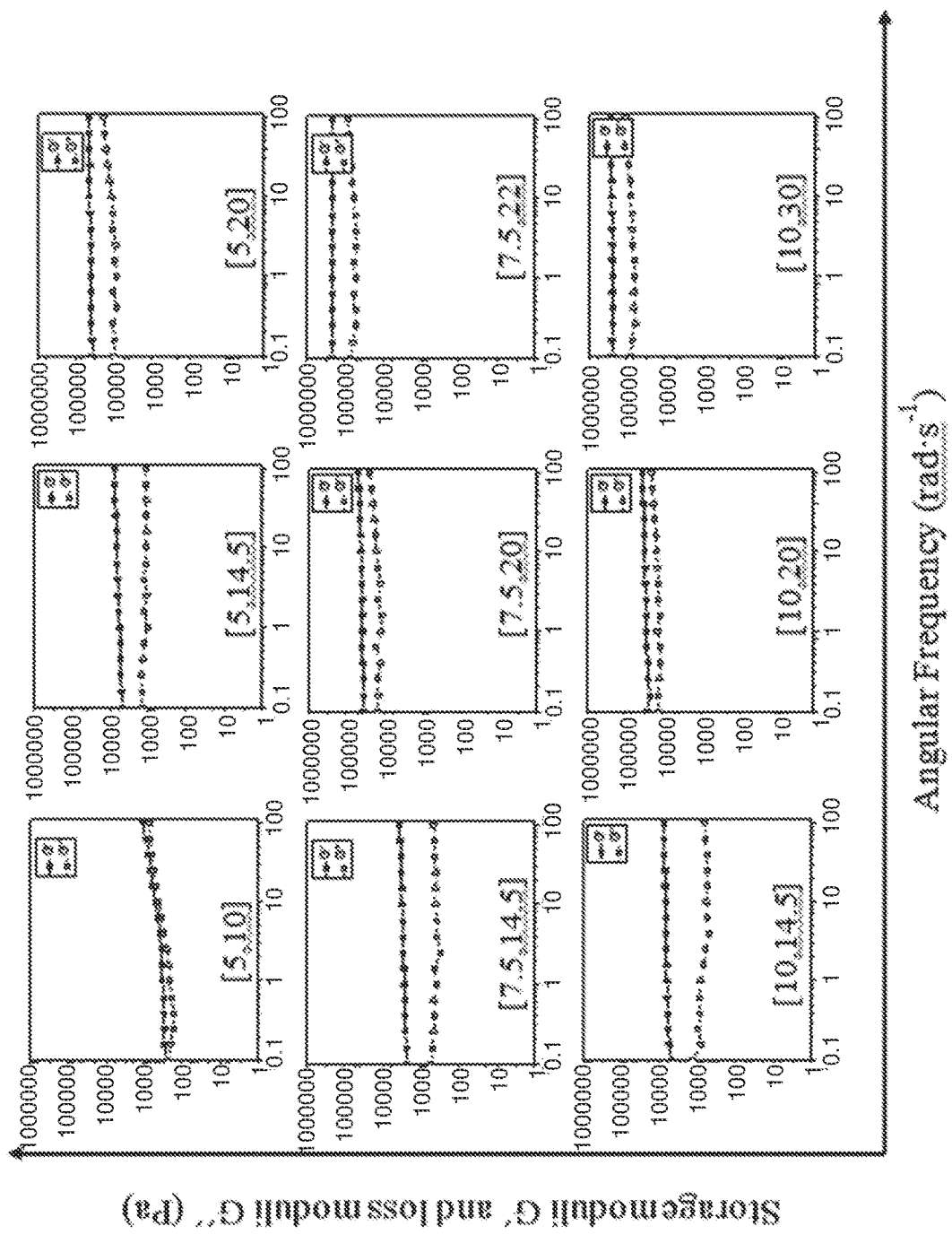
FIG. 12. Angular frequency sweep profiles of PRHs listed in FIG. 10.
Figure 13:
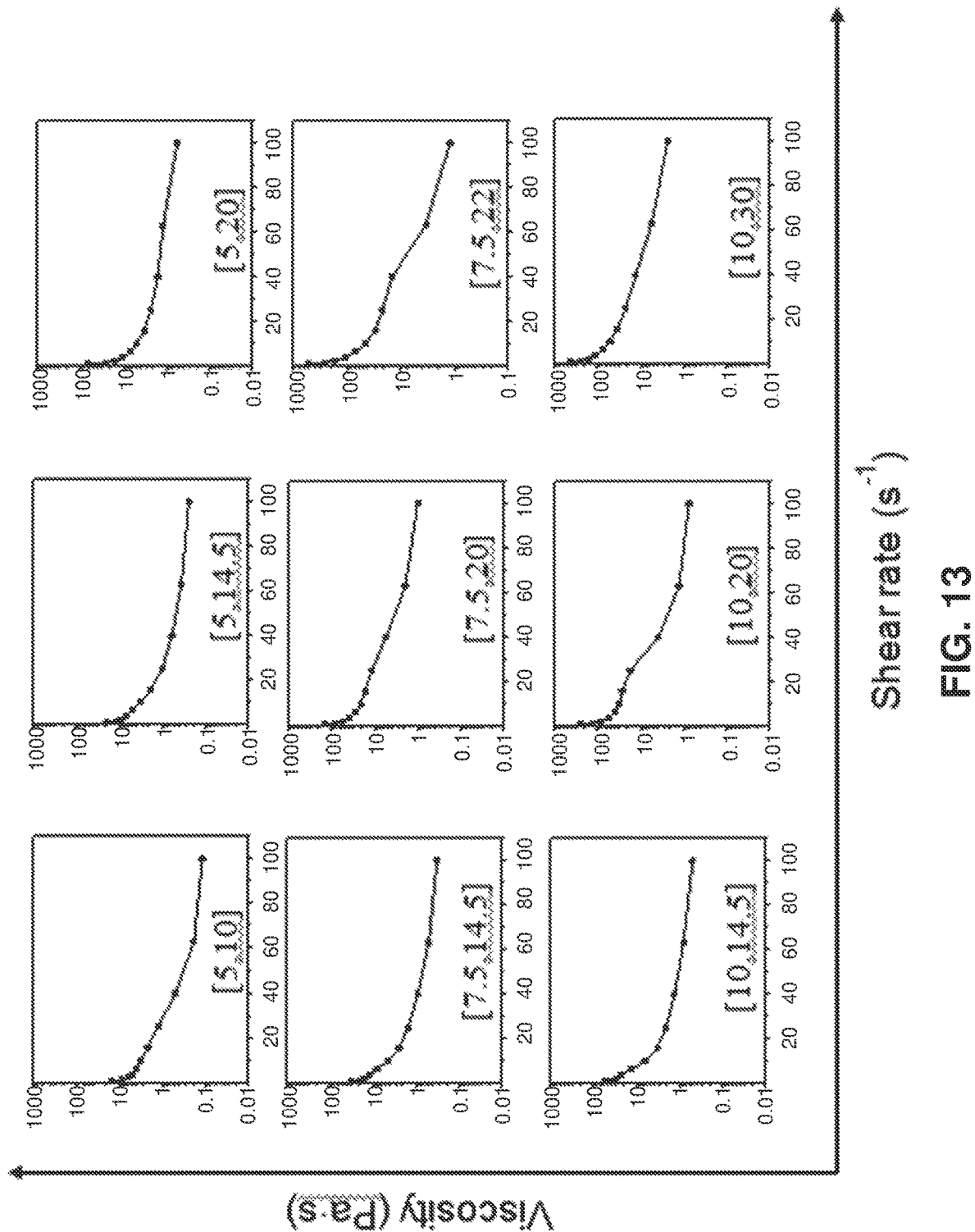
FIG. 13. Steady sheer sweep profiles of PRHs listed in FIG. 10.

Within the linear viscoelastic region, the elastic and loss moduli at room temperature were investigated by angular frequency sweep tests (FIG. 12). Except for PRH[5, 10], all PRHs possess frequency-independent moduli. Increasing the concentration of α-CD could effectively improve the PRHs' elastic properties. The fact that the PRHs are stable (G'>G") at different oscillation frequencies suggests that the assembly of polypseudorotaxanes and PPO blocks of F127 axle doesn't dynamically disassociate even at low frequencies.

Steady shear rate sweep experiments showed that all PRHs exhibit shear-thinning behaviors regardless of the concentration of α-CD and F127-MA$_2$. The viscosities of PRHs diminished dramatically (decreased to nearly 1/100) at high shear rate, rendering their extrudability during the process of direct-writing.

Figure 14:
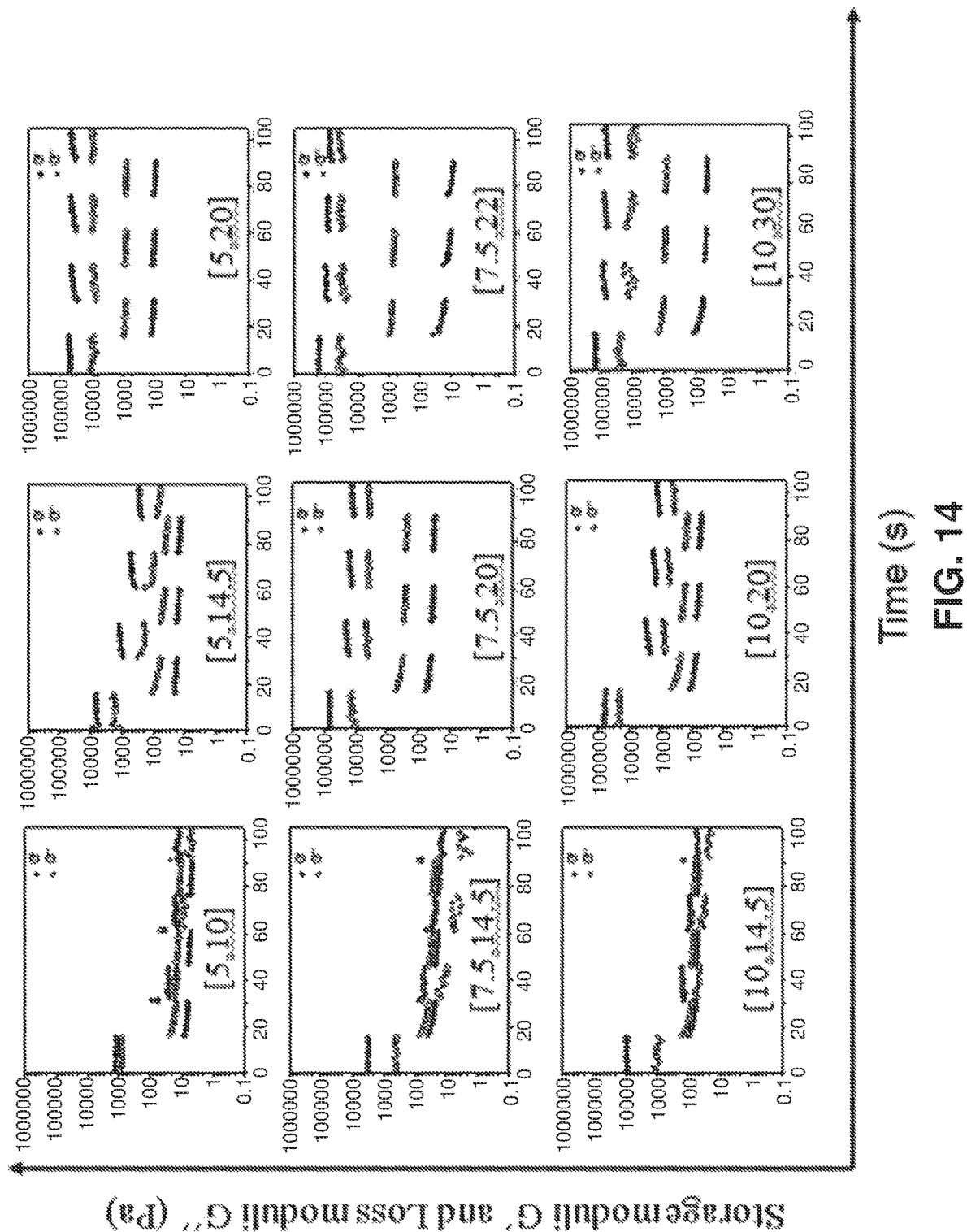
FIG. 14. Dynamic step-strain amplitude test profiles of PRHs listed in FIG. 10.

During the process of direct-writing, PRHs are extruded through printing tips, resulting in a large strain of samples. After extrusion, the printable materials are required to recover their mechanical strength rapidly to be self-supportive. Dynamic step-strain amplitude experiments were employed to investigate the self-healing capabilities of the PRHs. As shown in FIG. 14, after applying stress to result in 100% strain for 15 s, PRH[5, 10], PRH[7.5, 14.5] and PRH[10, 14.5] lost their viscoelastic properties significantly. PRH[5, 14.5], PRH[7.5, 20] and PRH[10, 20] could partially recover their viscoelastic properties while PRH[5, 20], PRH [7.5, 22] and PRH[10, 30] could effectively self-heal within 15 s.

By mapping the rheological properties of PRHs with the various amount of F127-MA$_2$ and α-CD, PRH[5, 20] was chosen as the optimized polypseudorotaxane hydrogel for 3-D printing tests as a result of the low yield strain=0.1%, high elastic modulus (40000 Pa), rapid self-healing capability.

S5. Direct-Write 3-D Printing and Post-Printing Polymerization

Methods: The prepared PRH was firstly loaded into a syringe barrel, centrifuged to remove the air bubbles and transferred into a Nordson EFD syringe barrel (3 mL) for direct-writing. Direct-writing experiments were performed on an extrusion-based 3-D printer (Tabletop, nScrypt) equipped with Nordson EFD precision smoothflower tapered tips (i.d.=400 μm). Printing paths were generated using the P-CAD software. Woodpile lattice cubes consisted of four repetitive layers were printed with good structural integrity.

S5.1 Photo-crosslinking of the printed monoliths. After direct-writing, the obtained lattice cubes were irradiated under a UV lamp (365 nm) for 4 h, resulting in photo-crosslinked polyrotaxane monoliths (PMs). After crosslinking, the lattice cubes were washed with an excess of DMSO and H$_2$O for 24 h respectively. Each step was repeated 3 times to remove the unreacted F127-MA$_2$, DMPA, VP and free CD or CD rings which are threaded on the unstopped F127 axle. Elemental analysis suggests 19±5 CD rings per F127 axle. Sample 1, calc: $(C_{603}H_{1200}O_{267})\cdot(C_{36}H_{60}O_{30})_{14.25}\cdot(C_6H_9NO)_{1.8}$. C: 50.52%, H: 7.79%, N: 0.09%; found: C: 50.46%, H: 7.86%, N: 0.16%. Sample 2, calc: $(C_{603}H_{1200}O_{267})\cdot(C_{361}H_6O_{30})_{24.15}\cdot(C_6H_9NO)_{1.8}\cdot(H_2O)_{42.2}$. C: 47.83%, H: 7.45%, N: 0.00%; found: C: 47.75%, H: 7.53%, N: 0.08%.

S5.2 Synthesis of polyrotaxane monoliths (PM$_{NMR}$) with low cross-linking degrees. In order to confirm the formation of polyrotaxane and calculate the α-CD ring threading ratio, three of PM$_{NMRS}$ with low 7.79%, N: 0.09%; found: C: 50.46%, H: 7.86%, N: 0.16%. Sample 2, calc: $(C_{603}H_{1200}O_{267})\cdot(C_{36}H_{60}O_{30})_{24.15}\cdot(C_6H_9NO)_{1.8}\cdot(H_2O)_{42.2}$. C: 47.83%, H: 7.45%, N: 0.00%; found: C: 47.75%, H: 7.53%, N: 0.08%.

S5.2 Synthesis of polyrotaxane monoliths (PM$_{NMR}$) with low cross-linking degrees. In order to confirm the formation of polyrotaxane and calculate the α-CD ring threading ratio, three of PM$_{NMRS}$ with low cross-linking degrees were prepared by reducing the photo-irradiation time. After direct-writing, three lattice cubes were photo-irradiated for 20, 40 and 60 min, respectively. The obtained lattice cubes were washed extensively with a large excess of water. After washing, these cubes lost their 3-D structure with significant weight loss recorded. Compared to PMs with higher cross-linking degrees, PM$_{NMRS}$ are soluble in DMSO, which are suitable for NMR analysis. We noticed some insoluble residues (PM with a higher crosslinking degree) in the DMSO-d$_6$ solution and it was removed before NMR experiments.

The synthesis of PM$_{NMR}$ with low degrees of cross-linking have been repeated three times and the obtained PM$_{NMR}$ were washed extensively with water to remove the unthreaded CD rings before the NMR experiment. However, set A α-CDs proton resonances were consistently observed in the $^1$H NMR experiments and the ratios between set A/B proton resonances are only dependent on the photoirradiation conditions.

S5.3 Synthesis of monolith M[5, 0]: Telechelic polymer F127-MA$_2$ (0.5 g, 0.04 mmol) was dissolved in water (10 mL) and a DMPA (24 mg, 0.094 mmol) in VP (40 μL) solution was added. The obtained solution was irradiated under a UV lamp (365 nm) for 4 h, affording a semi-transparent hydrogel M[5,0]. After crosslinking, the obtained M[5, 0] was washed with an excess of DMSO and H$_2$O for 24 h respectively, and each step had been repeated 3 times.

S6. Powder X-Ray Diffraction Measurements

Powder X-ray diffraction (PXRD) measurements were performed using a Bruker D8-Focus diffractometer fitted with Ni-filtered Cu Kα radiation. The voltage was set to 40 kV, and the current was 40 mA. The detector collected data over the range 2θ=5-30°. F127 was dissolved in distilled water and lyophilized as the powder form for PXRD measurement. PM was washed by an excess of DMSO and water to remove the free α-CD and lyophilized as the powder form. PRH[5, 20] was lyophilized as the powder form.

As shown above, both PM and PRH[5, 20] displayed characteristic diffractions at 2θ=7.2, 12.7, 19.6 and 22.3°, which were assigned to the {100}, {110}{210} {300} reflection from the hexagonal lattice with unit cell parameters a=b=13.65 Å according to the literature.[I. N. Topchieva, A. E. Tonelli, I. G. Panova, E. V. Matuchina, F. A. Kalashnikov, V. I. Gerasimov, C. C. Rusa, M. Rusa, M. A. Hunt, Langmuir 2004, 20, 9036-9043.].

S7. Shape Changing and Recovery Experiments

PM hydrogel to DMSO-gel: A PM was soaked in DMSO (30 mL) for solvent exchange. During this process, DMSO was refreshed every 6 h. After 24 h incubation, the PM hydrogel was converted to a DMSO-gel. PM DMSO-gel to hydrogel: A PM DMSO gel was soaked in water (30 mL) and the PM-hydrogel with the original 3-D structure was rebuilt within 2 h. These shape changing and recovery experiments have been repeated for 5 times.

S7.1. Rheological Studies of PM and M[5, 0] in Different Solvents

The storage and loss moduli of PM and M[5, 0] were measured by angular frequency sweep experiments in their DMSO-gel or hydrogel forms at 25° C. Both samples were prepared in molds to match the diameter of the parallel plate. The angular frequency applied to the sample was increased from 0.1 rad/s to 100 rad/s (frequency increased from 0.016 Hz to 15.92 Hz). The oscillation strain was set as 0.1%.

S7.2. Lifting Experiments

Coin-lifting experiment: A PM DMSO-gel was prepared after a solvent exchange and a US dime coin of 2.268 g was laid on top of the PM DMSO-gel. An excess of water was added to perform the solvent exchange and the heights of the coin at different time were recorded until the system was steady. The work of the PM performed was calculated using the equation W=mgΔh−μgVΔh, where m is the weight of the coin, p is the density of the water, g is gravitational acceleration constant, Δh is the height of the coin between initial and steady states, and V is the volume of the coin. After solvent exchange, the US dime coin was lifted 1.6 mm vertically. Based on the equation W=mgΔh−μgVΔh, about 30.5 μJ mechanical work was performed in this process.

Aluminum plate-lifting experiment: A PM DMSO-gel was freshly prepared after a solvent exchange and an aluminum plate of 0.309 g was laid on top of the PM. An excess of water was added to exchange the solvent and the heights of the aluminum plate at different times were recorded. After the solvent exchange, the aluminum plate was lifted 2.6 mm vertically. Based on the equation W=mgΔh−μgVΔh, about 2.34 μJ mechanical work was performed during this process.

Results and Discussion

When the applied external mechanical strain is large, the elasticity enhancement of the hydrogel induced by the ring-shutting motion is not capable of fully compensating this external energy, therefore the PM cannot recover to its original shape. Due to the elastic nature of the PM, the extra energy is stored as potential energy in the compressed (or other shape depending on the shape strain, compared to the original object) PM network. During the second stage of shape changing, the polyrotaxane arrays interact to form crystalline domains via cooperative multivalent hydrogen bonding interactions. After the removal of the external strain, the formed hydrogen bonding network in the polyrotaxane monolith is strong enough to keep the temporary shape as a result of the high kinetic energy barrier in breaking the hydrogen bonding network. During the second solvent exchange cycle, this meta-stable network is disrupted by solvation, thus can recover to its original thermodynamically favorable shape.

As shown in FIG. 21, a M[5, 0] dry gel uptakes 41 and 45 times (by mass ratio) of DMSO and $H_2O$, respectively. In comparison, PM only uptakes 21 times of $H_2O$ in its hydrogel form, suggesting that the hydrogen bonding network formed between α-CD rings on the polyrotaxane reduces the void spaces in the PM hydrogel. Breaking these hydrogen bonding interactions using DMSO could enable the ring shuttling motions, which allows α-CD rings and F127 axles to be extensively solvated in the PM.

Example 2. pH Responsive 3-D Printed Monolith

Figure 22:
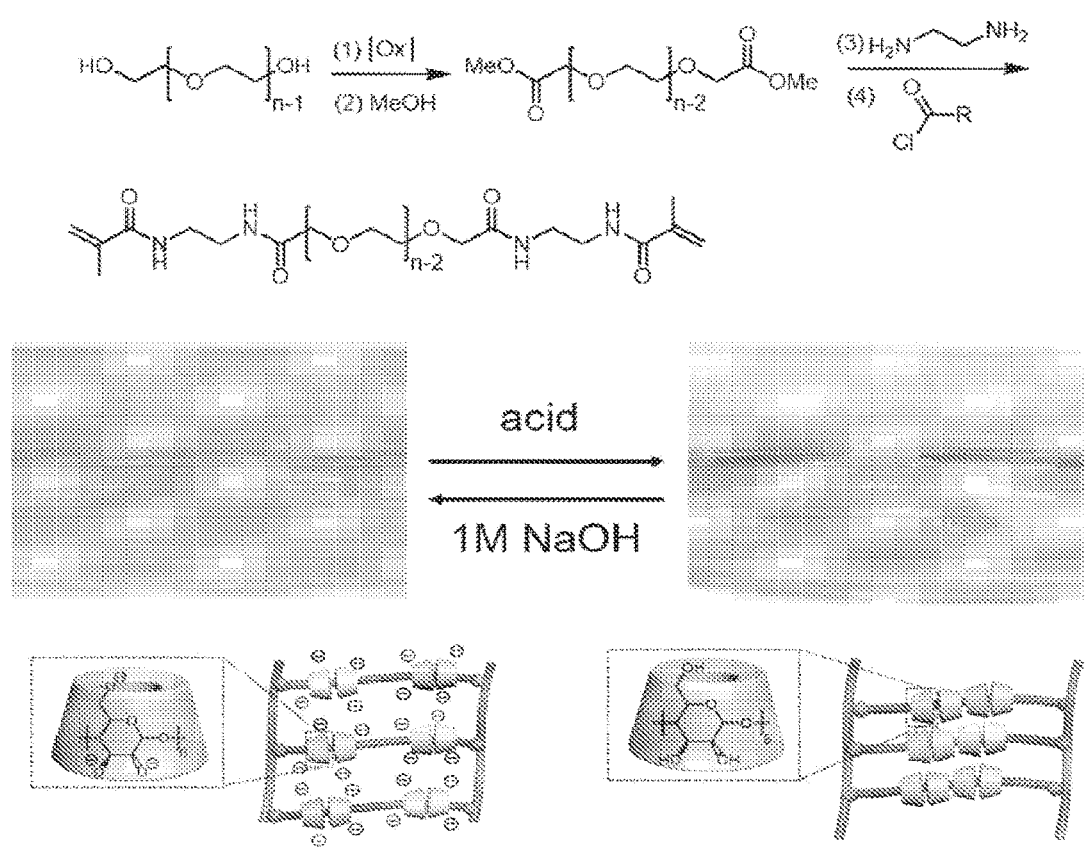
FIG. 22. Shows graphical illustration of synchronized ring motions through inter-ring and inter-tubular communication via change in pH.

It has been reported that the primary hydroxyl groups of α-CD will be deprotonated above pH 12. When a 3-D-printed PM is soaked in water, simply increasing the environment pH>12 (FIG. 22) will disrupt the primary face inter-ring interaction, forming ring dimers that could in principle shuttle along the polymer backbone. PEO-AMA$_2$ was employed as the polymer backbone for the pH switching investigations. A pH dependent rheology test was performed to study the PM elastic moduli in response to pH increase. As shown in FIG. 22, the 3-D printed monolith quickly switched between the deformed and reformed states.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, including any isomers, enantiomers and diastereomers of the group members, are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

Many of the molecules disclosed herein contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Every formulation or combination of components described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

REFERENCES

[1] a) J.-P. Sauvage, C. Dietrich-Buchecker, Molecular catenanes, rotaxanes and knots: a journey through the world of molecular topology, Wiley, Hoboken, 2008; b) C. J. Bruns, J. F. Stoddart, The Nature of the Mechanical Bond: From Molecules to Machines, Wiley, Hoboken, 2016.

[2] a) H. Tian, Q.-C. Wang, Chem. Soc. Rev. 2006, 35, 361-374; b) K. D. H-nni, D. A. Leigh, Chem. Soc. Rev. 2010, 39, 1240-1251; c) J. E. Beves, B. A. Blight, C. J. Campbell, D. A. Leigh, R. T. McBurney, Angew. Chem. Int. Ed. 2011, 50, 9260-9327; Angew. Chem. 2011, 123, 9428-9499; d) T. Ogoshi, T. Aoki, R. Shiga, R. Iizuka, S. Ueda, K. Demachi, D. Yamafuji, H. Kayama, T.-a. Yamagishi, J. Am. Chem. Soc. 2012, 134, 20322-20325; e) S. Lee, C.-H. Chen, A. H. Flood, Nat. Chem. 2013, 5, 704-710; f) M. Xue, Y. Yang, X. Chi, X. Yan, F. Huang, Chem. Rev. 2015, 115, 7398-7501; g) Z. Chen, D. Aoki, S. Uchida, H. Marubayashi, S. Nojima, T. Takata, Angew. Chem. Int. Ed. 2016, 55, 2778-2781; Angew. Chem. 2016, 128, 2828-2831.

[3] a) A. Harada, J. Li, M. Kamachi, Nature 1992, 356, 325-327; b) Y. Okumura, K. Ito, Adv. Mater. 2001, 13, 485-487; c) G. Wenz, B.-H. Han, A. Mgller, Chem. Rev. 2006, 106, 782-817; d) A. Harada, A. Hashidzume, H. Yamaguchi, Y. Takashima, Chem. Rev. 2009, 109, 5974-6023; e) T. Ogoshi, T. Aoki, S. Ueda, Y. Tamura, T.-a. Yamagishi, Chem. Commun. 2014, 50, 6607-6609.

[4] a) C. O. Dietrich-Buchecker, J. P. Sauvage, J. P. Kintzinger, Tetrahedron Lett. 1983, 24, 5095-5098; b) T. Ogoshi, T. Akutsu, D. Yamafuji, T. Aoki, T. A. Yamagishi, Angew. Chem. Int. Ed. 2013, 52, 8111-8115; Angew. Chem. 2013, 125, 8269-8273; c) G. Gil-Ram&rez, D. A.

Leigh, A. J. Stephens, Angew. Chem. Int. Ed. 2015, 54, 6110-6150; Angew. Chem. 2015, 127, 6208-6249.

[5] a) R. S. Forgan, J.-P. Sauvage, J. F. Stoddart, Chem. Rev. 2011, 111, 5434-5464; b) J. F. Ayme, J. E. Beves, D. A. Leigh, R. T. McBurney, K. Rissanen, D. Schultz, Nat. Chem. 2012, 4, 15-20; c) J.-F. Ayme, J. E. Beves, C. J. Campbell, D. A. Leigh, Chem. Soc. Rev. 2013, 42, 1700-1712.

[6] a) R. A. Bissell, E. Clrdova, A. E. Kaifer, J. F. Stoddart, Nature 1994, 369, 133-137; b) H. Murakami, A. Kawabuchi, K. Kotoo, M. Kunitake, N. Nakashima, J. Am. Chem. Soc. 1997, 119, 7605-7606; c) P. R. Ashton, R. Ballardini, V. Balzani, I. Baxter, A. Credi, M. C. Fyfe, M. T. Gandolfi, M. Glmez-Llpez, M.-V. Martinez-Diaz, A. Piersanti, J. Am. Chem. Soc. 1998, 120, 11932-11942; d) J. D. Crowley, S. M. Goldup, A.-L. Lee, D. A. Leigh, R. T. McBurney, Chem. Soc. Rev. 2009, 38, 1530-1541; e) C.-F. Lee, D. A. Leigh, R. G. Pritchard, D. Schultz, S. J. Teat, G. A. Timco, R. E. Winpenny, Nature 2009, 458, 314-318.

[7] a) B. L. Feringa, W. R. Browne, Molecular Switches, Vol. 42, Wiley Online Library, Hoboken, 2001; b) X. Su, I. Aprahamian, Chem. Soc. Rev. 2014, 43, 1963-1981.

[8] C. J. Bruns, J. F. Stoddart, Acc. Chem. Res. 2014, 47, 2186-2199.

[9] C. Cheng, P. R. McGonigal, S. T. Schneebeli, H. Li, N. A. Vermeulen, C. Ke, J. F. Stoddart, Nat. Nanotechnol. 2015, 10, 547-553.

[10] a) J. Bern #, D. A. Leigh, M. Lubomska, S. M. Mendoza, E. M. Perez, P. Rudolf, G. Teobaldi, F. Zerbetto, Nat. Mater. 2005, 4, 704-710; b) Y. Liu, A. H. Flood, P. A. Bonvallet, S. A. Vignon, B. H. Northrop, H.-R. Tseng, J. O. Jeppesen, T. J. Huang, B. Brough, M. Bailer, S. Magonov, S. D. Solares, W. A. Goddard, C.-M. Ho, J. F. Stoddart, J. Am. Chem. Soc. 2005, 127, 9745-9759.

[11] W. R. Browne, B. L. Feringa, Nat. Nanotechnol. 2006, 1, 25-35.

[12] R. Eelkema, M. M. Pollard, J. Vicario, N. Katsonis, B. S. Ramon, C. W. Bastiaansen, D. J. Broer, B. L. Feringa, Nature 2006, 440, 163-163.

[13] A. Coskun, M. Banaszak, R. D. Astumian, J. F. Stoddart, B. A. Grzybowski, Chem. Soc. Rev. 2012, 41, 19-30.

[14] K. Iwaso, Y. Takashima, A. Harada, Nat. Chem. 2016, 8, 625-632.

[15] Q. Li, G. Fuks, E. Moulin, M. Maaloum, M. Rawiso, I. Kulic, J. T. Foy, N. Giuseppone, Nat. Nanotechnol. 2015, 10, 161-165.

[16] a) N. Koumura, R. W. Zijlstra, R. A. van Delden, N. Harada, B. L. Feringa, Nature 1999, 401, 152-155; b) R. A. Van Delden, M. K. Ter Wiel, M. M. Pollard, J. Vicario, N. Koumura, B. L. Feringa, Nature 2005, 437, 1337-1340; c) N. Ruangsupapichat, M. M. Pollard, S. R. Harutyunyan, B. L. Feringa, Nat. Chem. 2011, 3, 53-60.

[17] D. Aoki, S. Uchida, T. Takata, Angew. Chem. Int. Ed. 2015, 54, 6770-6774; Angew. Chem. 2015, 127, 6874-6878.

[18] a) A. Harada, R. Kobayashi, Y. Takashima, A. Hashidzume, H. Yamaguchi, Nat. Chem. 2011, 3, 34-37; b) S. Iamsaard, S. J. Aßhoff, B. Matt, T. Kudernac, J. J. Cornelissen, S. P. Fletcher, N. Katsonis, Nat. Chem. 2014, 6, 229-235.

[19] I. Gibson, D. W. Rosen, B. Stucker, Additive Manufacturing Technologies: 3DPrinting, Rapid Prototyping and Direct Digital Manufacturing, 2nd ed., Springer, New York, 2015.

[20] a) J. A. Lewis, Adv. Funct. Mater. 2006, 16, 2193-2204; b) M. Zhang, A. Vora, W. Han, R. J. Wojtecki, H. Maune, A. Le, L. E. Thompson, G. M. McClelland, F. Ribet, A. C. Engler, A. Nelson, Macromolecules 2015, 48, 6482-6488.

[21] a) D. B. Kolesky, K. A. Homan, M. A. Skylar-Scott, J. A. Lewis, Proc. Natl. Acad. Sci. USA 2016, 113, 3179-3184; b) J. M. McCracken, A. Badea, M. E. Kandel, A. S. Gladman, D. J. Wetzel, G. Popescu, J. A. Lewis, R. G. Nuzzo, Adv. Healthcare Mater. 2016, 5, 1025-1039.

[22] C. Zhu, T. Y. Han, E. B. Duoss, A. M. Golobic, J. D. Kuntz, C. M. Spadaccini, M. A. Worsley, Nat. Commun. 2015, 6, 6962.

[23] a) B. Y. Ahn, E. B. Duoss, M. J. Motala, X. Guo, S. I. Park, Y. Xiong, J. Yoon, R. G. Nuzzo, J. A. Rogers, J. A. Lewis, Science 2009, 323, 1590-1593; b) K. Sun, T.-S. Wei, B. Y. Ahn, J. Y. Seo, S. J. Dillon, J. A. Lewis, Adv. Mater. 2013, 25, 4539-4543.

[24] J. R. Raney, J. A. Lewis, MRS Bull. 2015, 40, 943-950.

[25] T. Jungst, W. Smolan, K. Schacht, T. Scheibel, J. Groll, Chem. Rev. 2016, 116, 1496-1539.

[26] A. Harada, J. Li, M. Kamachi, Macromolecules 1993, 26, 5698-5703.

[27] A. Harada, J. Li, M. Kamachi, Macromolecules 1994, 27, 4538-4543.

[28] M. Ceccato, P. Lo Nostro, P. Baglioni, Langmuir 1997, 13, 2436-2439.

[29] Y. Yu, W. Cai, C. Ch Chipot, T. Sun, X. Shao, J. Phys. Chem. B 2008, 112, 5268-5271 [30] K. A. Udachin, L. D. Wilson, J. A. Ripmeester, J. Am. Chem. Soc. 2000, 122, 12375-12376.

[31] N. Yui, T. Ooya, T. Kumeno, Bioconjugate Chem. 1998, 9, 118-125.

[32] M. Y. Kozlov, N. S. Melik-Nubarov, E. V. Batrakova, A. V. Kabanov, Macromolecules 2000, 33, 3305-3313.

[33] F. Cacialli, J. S. Wilson, J. J. Michels, C. Daniel, C. Silva, R. H. Friend, N. Severin, P. Samor', J. P. Rabe, M. J. O'Connell, P. N. Talyor, H. L. Anderson, Nat. Mater. 2002, 1, 160-164.

[34] a) T. Arai, K. Jang, Y. Koyama, S. Asai, T. Takata, Chem. Eur. J. 2013, 19, 5917-5923; b) J. Sawada, D. Aoki, S. Uchida, H. Otsuka, T. Takata, ACS Macro Lett. 2015, 4, 598-601.

[35] C. Pradal, K. S. Jack, L. Grondahl, J. J. Cooper-White, Biomacromolecules 2013, 14, 3780-3792.

[36] V. Mucci, C. Vallo, J. Appl. Polym. Sci. 2012, 123, 418-425.

[37] D. Ma, X.-Y. Zhou, Y.-F. Yang, Y. You, Z.-H. Liu, J.-T. Lin, T. Liu, W. Xue, Sci. Adv. Mater. 2013, 5, 1307-1315.

[38] C. Travelet, G. Schlatter, P. H8braud, C. Brochon, A. Lapp, D. V. Anokhin, D. A. Ivanov, C. Gaillard, G. Hadziioannou, Soft Matter 2008, 4, 1855-1860.

[39] Although these PRHs could not recover their elastic moduli rapidly, they could recover their viscoelastic properties after 4-12 hours.

[40] I. N. Topchieva, A. E. Tonelli, I. G. Panova, E. V. Matuchina, F. A. Kalashnikov, V. I. Gerasimov, C. C. Rusa, M. Rusa, M. A. Hunt, Langmuir 2004, 20, 9036-9043.

[41] H. Meng, G. Li, J. Mater. Chem. A 2013, 1, 7838-7865.

What is claimed is:
1. A method of manufacturing a supramolecular polypseudorotaxane hydrogel composition capable of reversible 3-D structural deformation, said method comprising:
mixing a solvent, an at least partially linear co-polymer, and a plurality of macrocyclic rings, and:

covalently cross-linking the at least partially linear co-polymer to form a crosslinked polymer network comprising the pseudorotaxane,
   wherein the at least partially linear co-polymer comprises groups capable of covalent crosslinking between the at least partially linear co-polymers,
   wherein the macrocyclic rings comprise first macrocyclic rings that form a pseudorotaxane in the composition, and second macrocyclic rings that do not form a pseudorotaxane in the composition, and
   wherein the hydrogel composition has a viscosity which allows for 3-D printing of the hydrogel to form a 3-D structure, and an elastic modulus after crosslinking that allows for the 3-D structure to undergo reversible 3-D structural deformation upon change of solvent conditions.

2. The method of claim 1, wherein the covalent cross-linking comprises a free radical reaction or a condensation reaction.

3. The method of claim 1, wherein the covalent cross-linking comprises a photo-initiated free radical reaction.

4. The method of claim 1, wherein the at least partially linear co-polymer is in an amount from about 1 to about 20% w/v of the composition.

5. The method of claim 1, wherein the at least partially linear co-polymer is an amphiphilic or hydrophilic polymer.

6. The method of claim 1, wherein the at least partially linear co-polymer is a nonionic amphiphilic polymer.

7. The method of claim 6, wherein the nonionic amphiphilic polymer is present at a concentration above its critical micellular concentration (cmc).

8. The method of claim 6, wherein the nonionic amphiphilic polymer is a copolymer comprising at least one block of lesser hydrophilicity and at least one hydrophilic block.

9. The method of claim 6, wherein the nonionic amphiphilic polymer is a copolymer comprising at least one central block of lesser hydrophilicity and at least two terminal hydrophilic blocks.

10. The method of claim 9, wherein the hydrophilic blocks are selected from the group consisting of polyethylene oxide (PEO), polyethylene imide, and polyvinyl alcohol.

11. The method of claim 9, wherein the block of lesser hydrophilicity is selected from the group consisting of polypropylene oxide (PPO), polydimethylsiloxane (PDMS), polystyrene, and polycaprolactone (PCL).

12. The method of claim 6, wherein the nonionic amphiphilic polymer is a copolymer comprising poly(ethylene oxide) and poly(propylene oxide).

13. The method of claim 12, wherein the at least partially linear co-polymer is present in an amount of about 7.5% w/v of the composition.

14. The method of claim 1, wherein the at least partially linear co-polymer is a nonionic hydrophilic polymer.

15. The method of claim 14, wherein the nonionic hydrophilic polymer is a polymer or copolymer comprising poly(ethylene oxide).

16. A method of manufacturing a supramolecular polypseudorotaxane hydrogel composition capable of reversible 3-D structural deformation, said method comprising:
   mixing a solvent, an at least partially linear co-polymer, and a plurality of macrocyclic rings,
   wherein the at least partially linear co-polymer comprises groups capable of covalent crosslinking between the at least partially linear co-polymers,
   wherein the groups capable of covalent crosslinking between the at least partially linear co-polymers comprise N-aminoethyl-methylacrylamide,
   wherein the macrocyclic rings comprise first macrocyclic rings that form a pseudorotaxane in the composition, and second macrocyclic rings that do not form a pseudorotaxane in the composition, and
   wherein the hydrogel composition has a viscosity which allows for 3-D printing of the hydrogel to form a 3-D structure, and an elastic modulus after crosslinking that allows for the 3-D structure to undergo reversible 3-D structural deformation upon change of solvent conditions.

17. The method of claim 1, wherein the first macrocyclic rings are present in an amount of from about 10 to about 30% w/v of the composition.

18. The method of claim 1, wherein the first macrocyclic rings are present in an amount of from about 14.5 to about 25% w/v of the composition.

19. A method of manufacturing a supramolecular polypseudorotaxane hydrogel composition capable of reversible 3-D structural deformation, said method comprising:
   mixing a solvent, an at least partially linear co-polymer, and a plurality of macrocyclic rings,
   wherein the at least partially linear co-polymer comprises groups capable of covalent crosslinking between the at least partially linear co-polymers,
   wherein the macrocyclic rings comprise first macrocyclic rings that form a pseudorotaxane in the composition, and second macrocyclic rings that do not form a pseudorotaxane in the composition,
   wherein the first macrocyclic rings are present in an amount of from about 20 to about 35% w/v of the composition, and
   wherein the hydrogel composition has a viscosity which allows for 3-D printing of the hydrogel to form a 3-D structure, and an elastic modulus after crosslinking that allows for the 3-D structure to undergo reversible 3-D structural deformation upon change of solvent conditions.

20. The method of claim 1, wherein the macrocyclic rings comprise a cyclodextrin or a modified cyclodextrin derivative.

21. The method of claim 20, wherein the cyclodextrin is selected from the group consisting of a-cyclodextrin, b-cyclodextrin, and g-cyclodextrin.

22. The method of claim 20, wherein the cyclodextrin comprises a-cyclodextrin.

23. The method of claim 1, wherein the amount of the macrocyclic rings is in excess of the amount to form the pseudorotaxane.

24. A method of manufacturing a supramolecular polypseudorotaxane hydrogel composition capable of reversible 3-D structural deformation, said method comprising:
   mixing a solvent, an at least partially linear co-polymer, and a plurality of macrocyclic rings,
   wherein the at least partially linear co-polymer comprises groups capable of covalent crosslinking between the at least partially linear co-polymers,
   wherein the molar ratio of the at least partially linear co-polymer to the macrocyclic rings is about 30:1 to about 60:1,
   wherein the macrocyclic rings comprise first macrocyclic rings that form a pseudorotaxane in the composition, and second macrocyclic rings that do not form a pseudorotaxane in the composition, and
   wherein the hydrogel composition has a viscosity which allows for 3-D printing of the hydrogel to form a 3-D structure, and an elastic modulus after crosslinking that allows for the 3-D structure to undergo reversible 3-D structural deformation upon change of solvent conditions.

25. A method of manufacturing a supramolecular polypseudorotaxane hydrogel composition capable of reversible 3-D structural deformation, said method comprising:

mixing a solvent, an at least partially linear co-polymer, and a plurality of macrocyclic rings, wherein the at least partially linear co-polymer comprises groups capable of covalent crosslinking between the at least partially linear co-polymers, wherein the molar ratio of the at least partially linear co-polymer to the macrocyclic rings is about 35:1 to about 55:1, wherein the macrocyclic rings comprise first macrocyclic rings that form a pseudorotaxane in the composition, and second macrocyclic rings that do not form a pseudorotaxane in the composition, and wherein the hydrogel composition has a viscosity which allows for 3-D printing of the hydrogel to form a 3-D structure, and an elastic modulus after crosslinking that allows for the 3-D structure to undergo reversible 3-D structural deformation upon change of solvent conditions.

26. The method of claim 1, wherein the 3-D structure comprises internal cavities or voids that are interconnected in one, two or three dimensions within the structure.

27. A method of manufacturing a supramolecular polypseudorotaxane hydrogel composition capable of reversible 3-D structural deformation, said method comprising:

mixing a solvent, an at least partially linear co-polymer, and a plurality of macrocyclic rings, wherein the at least partially linear co-polymer comprises groups capable of covalent crosslinking between the at least partially linear co-polymers, wherein the macrocyclic rings comprise first macrocyclic rings that form a pseudorotaxane in the composition, and second macrocyclic rings that do not form a pseudorotaxane in the composition, and wherein the hydrogel composition has a viscosity which allows for 3-D printing of the hydrogel to form a 3-D structure, and an elastic modulus after crosslinking that allows for the 3-D structure to undergo reversible 3-D structural deformation upon change of solvent conditions, and wherein the formed hydrogel composition further comprises a plurality of hexagonal crystalline domains, wherein the hexagonal crystalline domains comprise non-covalent interactions between the plurality of first macrocyclic rings and second macrocyclic rings, and wherein the hexagonal crystalline domains are capable of rapidly and reversibly deforming and reforming after application and removal of an external mechanical force.

28. The method of claim 1, wherein the storage modulus of the hydrogel composition is between about 85 and 95 kPa.

29. A method of manufacturing a supramolecular polypseudorotaxane hydrogel composition capable of reversible 3-D structural deformation, said method comprising:

mixing a solvent, an at least partially linear co-polymer, and a plurality of macrocyclic rings, wherein the at least partially linear co-polymer comprises groups capable of covalent crosslinking between the at least partially linear co-polymers, wherein the macrocyclic rings comprise first macrocyclic rings that form a pseudorotaxane in the composition, and second macrocyclic rings that do not form a pseudorotaxane in the composition, and wherein the hydrogel composition has a viscosity which allows for 3-D printing of the hydrogel to form a 3-D structure, and an elastic modulus after crosslinking that allows for the 3-D structure to undergo reversible 3-D structural deformation upon change of solvent conditions, and wherein the viscosity of the hydrogel composition at a shear rate of $1\ s^{-1}$ and 25° C. is between 1 and 500 Pa·s.

* * * * *